(12) United States Patent
Castelli

(10) Patent No.: US 11,559,416 B2
(45) Date of Patent: Jan. 24, 2023

(54) PORTABLE AND HAND-HELD MEDICAL DEVICE CRIMPER

(71) Applicant: MEDTRONIC VASCULAR, INC., Santa Rosa, CA (US)

(72) Inventor: Brian Castelli, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 17/095,214

(22) Filed: Nov. 11, 2020

(65) Prior Publication Data

US 2021/0154035 A1 May 27, 2021

Related U.S. Application Data

(60) Provisional application No. 62/941,131, filed on Nov. 27, 2019.

(51) Int. Cl.
*B25B 27/00* (2006.01)
*A61F 2/95* (2013.01)
*B21D 39/04* (2006.01)

(52) U.S. Cl.
CPC .......... *A61F 2/9522* (2020.05); *B21D 39/048* (2013.01); *Y10T 29/53896* (2015.01); *Y10T 29/53996* (2015.01)

(58) Field of Classification Search
CPC ......... B25B 27/00; B25B 27/02; B25B 27/14; B23P 11/00; B23P 11/005; B23P 11/02
See application file for complete search history.

(56) References Cited

U.S. PATENT DOCUMENTS

| | | | | |
|---|---|---|---|---|
| 4,429,451 A * | 2/1984 | Angelico | ............. | H01R 43/015 29/566.4 |
| 4,862,580 A * | 9/1989 | Wang | .................... | B25B 27/146 81/DIG. 11 |
| 5,211,050 A * | 5/1993 | Gouveia | .............. | H01R 43/042 72/413 |
| 5,282,303 A * | 2/1994 | Schriever | ............. | A41H 37/006 29/243.517 |
| 6,151,950 A * | 11/2000 | Wilhelm | .............. | H01R 43/042 29/751 |
| 6,230,387 B1 * | 5/2001 | Gritters | .................... | G02B 6/25 29/566.4 |

(Continued)

*Primary Examiner* — Lee D Wilson
(74) *Attorney, Agent, or Firm* — Medler Ferro Woodhouse & Mills PLLC

(57) ABSTRACT

A crimper includes a first arm that includes a first crimper die that defines a first tapered channel. The crimper also includes a second arm coupled to the first arm at a pivot connection. The second arm includes a second crimper die that defines a second tapered channel. The pivot connection enables the first arm and the second arm to rotate about the pivot connection from an open state to a closed state. The first arm and second arm rotate at an angle relative to one another to allow loading of the expandable medical device into the first tapered channel or the second tapered channel and to allow positioning of the expandable medical device relative to a delivery device. When transitioning, the first tapered channel and the second tapered channel form a chamber that is configured to crimp the expandable medical device from the uncompressed state to the compressed state.

27 Claims, 18 Drawing Sheets

(56) References Cited

U.S. PATENT DOCUMENTS

2011/0219845 A1* 9/2011 Schurder .................. B25B 7/20
                                                    72/409.01
2014/0304959 A1* 10/2014 Gilbreath ............. B21D 39/046
                                                    29/237
2021/0154035 A1* 5/2021 Castelli ................. A61F 2/9522

* cited by examiner

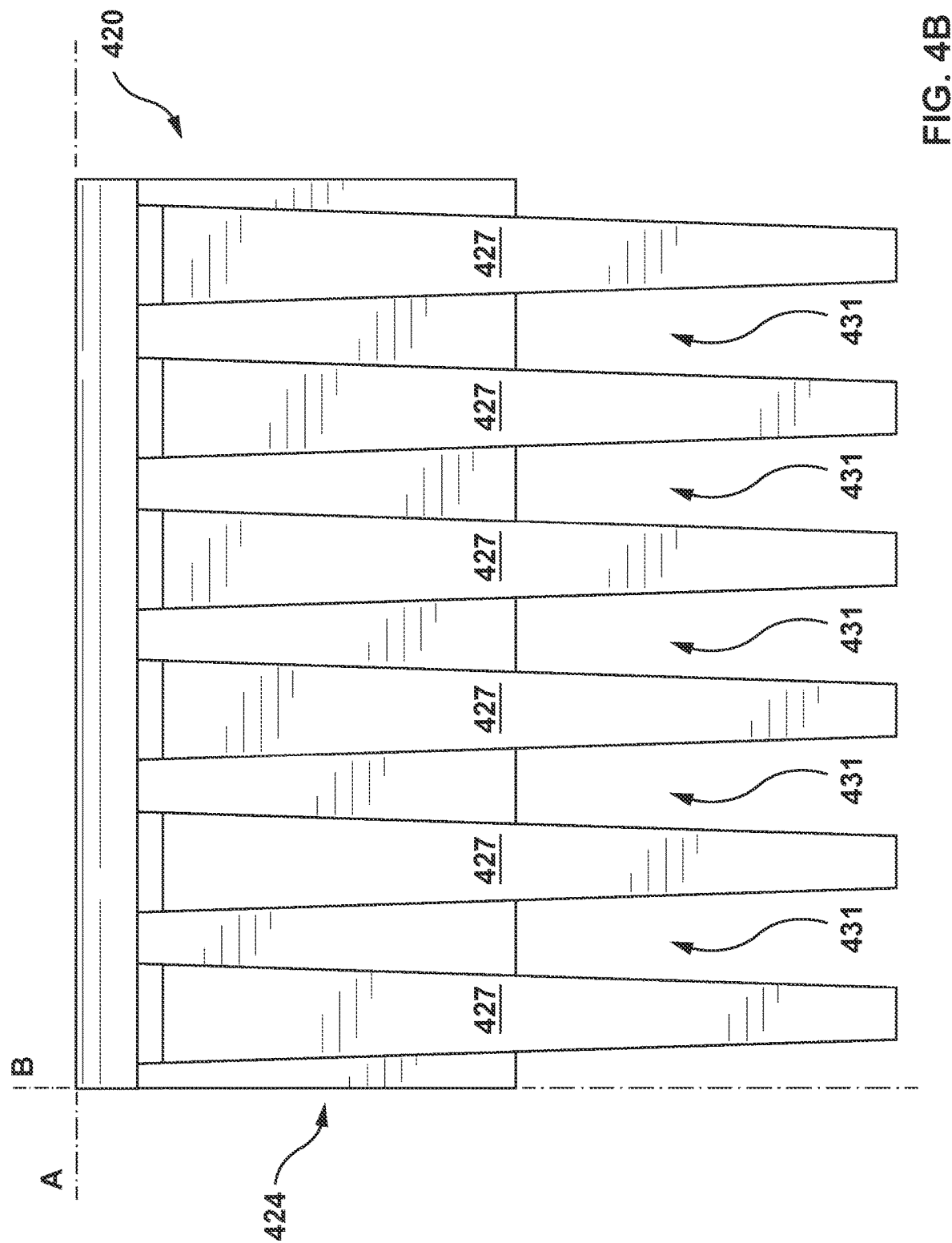

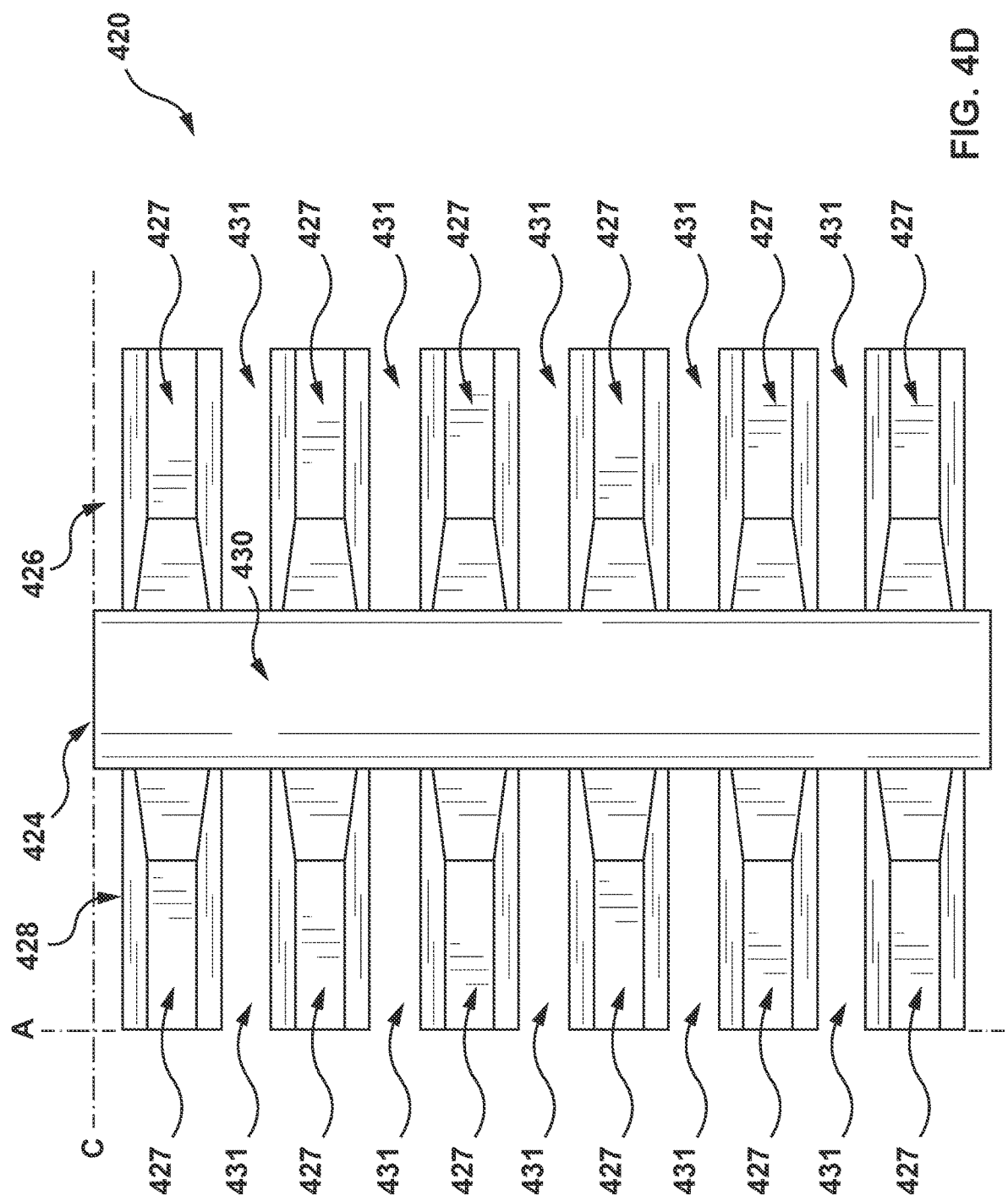

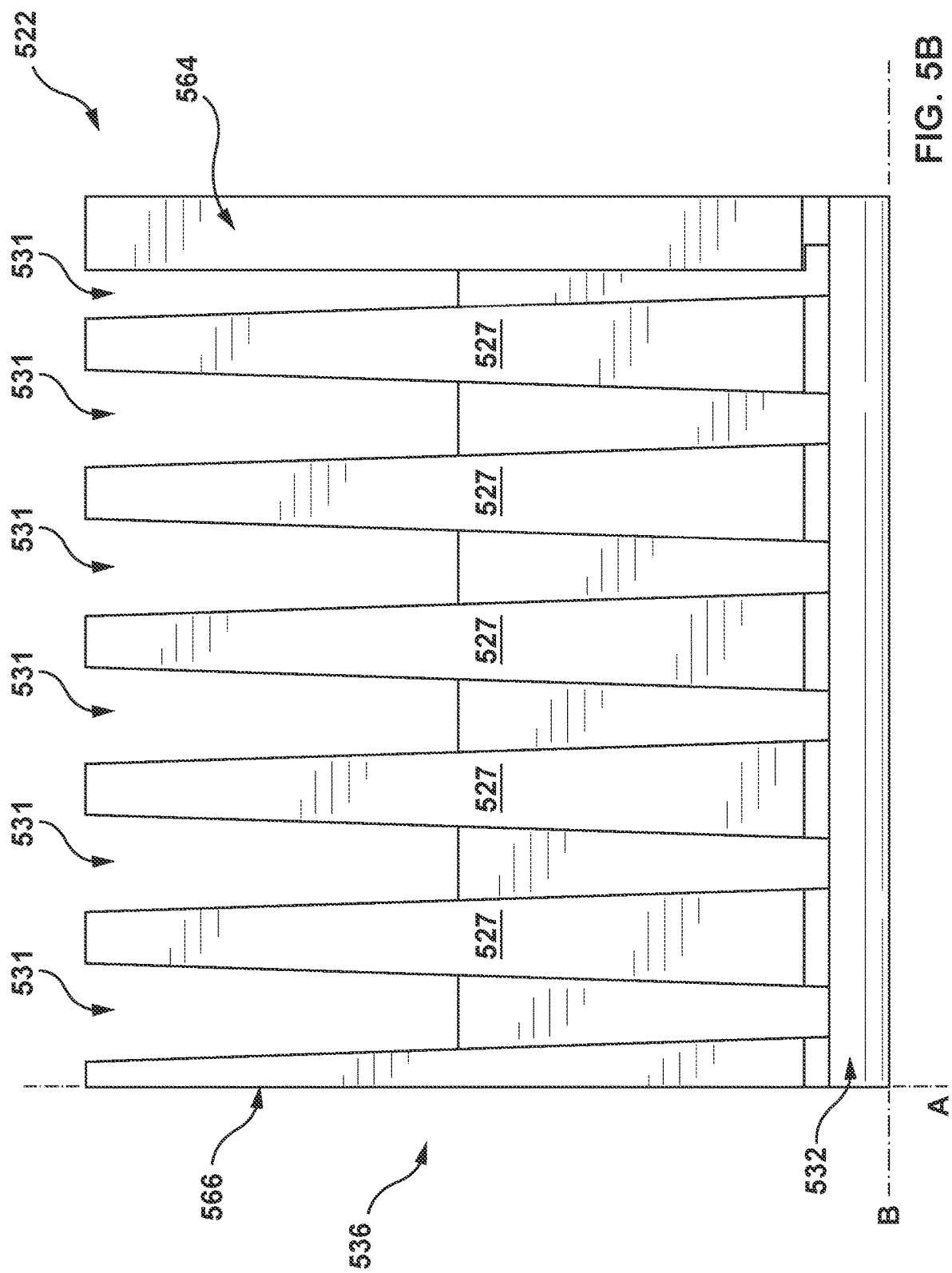

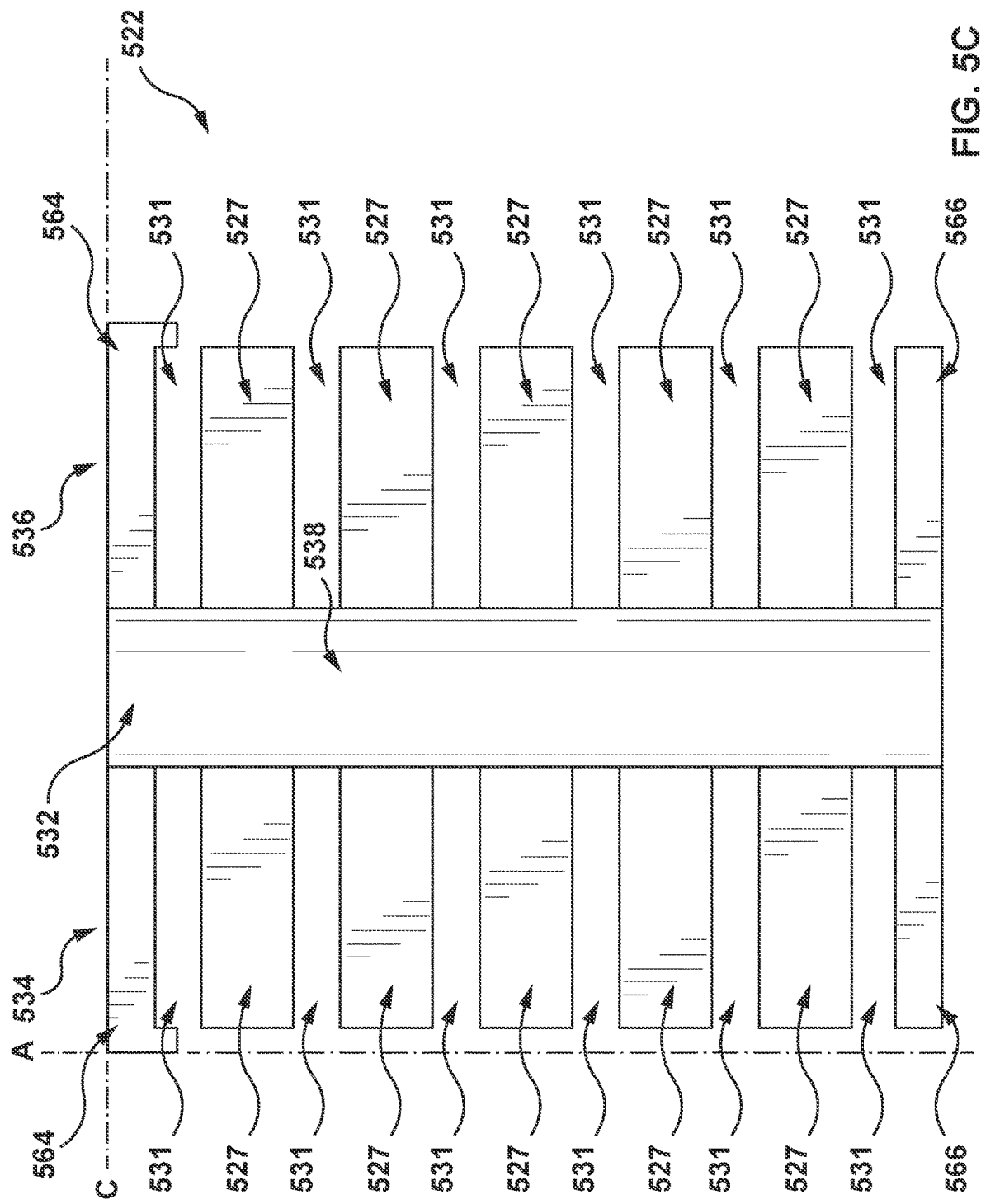

PORTABLE AND HAND-HELD MEDICAL DEVICE CRIMPER

PRIORITY

This application claims priority to U.S. Provisional Application No. 62/941,131 filed Nov. 27, 2019, the entire contents of which are incorporated by reference.

FIELD

The present technology is generally related to medical devices.

BACKGROUND

Currently, implantable medical devices and appliances, such as large stents, scaffolds, and other cardiac intervention devices that contain organic tissue, e.g., bovine and porcine, require onsite crimping onto a delivery device or appliance. This is due to the need to store the implantable devices in conditions specific to preserve the organic tissue. Typically, aftermarket iris style crimpers are utilized in the crimping processes. These iris style crimpers require a workstation that may be unwieldy and cost prohibitive due to their single use nature. Additionally, multiple crimping steps are sometimes necessary, and placement of the device in relation to marker bands or retaining features is difficult, which may require expensive, customized crimping equipment. Also, due to the complexity of the iris style crimping devices, sterilization of these single use devices may be difficult.

SUMMARY

The techniques of this disclosure generally relate to a crimper for loading an implantable medical device or appliance ("implantable medical device") onto a delivery device or appliance ("delivery device") and converting the implantable medical device from an uncompressed state to a compressed state. The crimper is designed to allow alignment and top loading of the implantable medical device. The crimper provides a portable solution for compressing and loading implantable medical devices at a location where the medical devices will be implanted. Further, the open, top loading design of the crimper provides increased visibility in loading and aligning the implantable medical devices and the delivery device as well as rapid fine adjustments. The design of the crimper and use of removable crimper dies reduces the work to clean and sterilize the crimper.

In one aspect, the present disclosure provides a crimper for altering an expandable medical device from an uncompressed state to a compressed state. The crimper includes a first arm that includes a first crimper die. The first crimper die defines a first tapered channel. The crimper also includes a second arm coupled to the first arm at a pivot connection. The second arm includes a second crimper die that defines a second tapered channel. The pivot connection enables the first arm and the second arm to rotate about the pivot connection from an open state to a closed state. When the first arm and the second arm are in the open state, the first arm and second arm rotate at an angle relative to one another to allow loading of the expandable medical device into the first tapered channel or the second tapered channel and to allow positioning of the expandable medical device relative to a delivery device. When the first arm and the second arm transition from the open state to the closed state, the first tapered channel and the second tapered channel form a chamber that is configured to crimp the expandable medical device from the uncompressed state to the compressed state.

In another aspect, the disclosure provides a crimper die unit for altering an expandable medical device from an uncompressed state to a compressed state. The crimper die unit includes a first crimper die. The first crimper die includes a base portion, a first row of crimper elements, and a second row of crimper elements. The base portion and the first and second rows of crimper elements of the first crimper die define a first tapered channel, and the first crimper die is configured to be coupled to a movable first arm of an arm unit. The crimper die unit also includes a second crimper die. The second crimper die comprises a base portion, a first row of crimper elements, and a second row of crimper elements. The base portion and the first and second rows of crimper elements of the second crimper die define a second tapered channel. The second crimper die is configured to be coupled to a movable second arm of the arm unit. The first crimper die and the second crimper die are arranged in the arm unit such that, when the arm unit is in an open state, the movable first arm and the movable second arm are positioned at an angle relative to one another to allow loading of the expandable medical device into the first tapered channel or the second tapered channel and to allow positioning of the expandable medical device relative to a delivery device. When the arm unit transitions from the open state to the closed state, the first and second rows of the crimper elements of the first crimper die are arranged to intermesh with the first and second rows of the crimper elements of the second crimper die such that the first tapered channel and the second tapered channel define a chamber that is configured to crimp the expandable medical device from the uncompressed state to the compressed state.

In another aspect, the disclosure provides a method for altering an expandable medical device from an uncompressed state to a compressed state. The method includes placing a crimper in an open state where the crimper includes a first crimper die defining a first tapered channel and a second crimper die defining a second tapered channel. In the open state, a top of the first tapered channel or a top of the second tapered channel is exposed for loading the expandable medical device. The method also includes loading the expandable medical device into the first tapered channel or the second tapered channel. Additionally, the method includes transitioning the crimper from the open state to a closed state, where transitioning the crimper from the open state to the closed state, the first tapered channel and the second tapered channel form a chamber that crimps the expandable medical device from the uncompressed state to the compressed state.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The foregoing and other features and advantages of the present disclosure will be apparent from the following description of embodiments hereof as illustrated in the accompanying drawings. The accompanying drawings, which are incorporated herein and form a part of the specification, further serve to explain the principles of the present disclosure and to enable a person skilled in the pertinent art to make and use the embodiments of the present disclosure. The drawings are not to scale.

FIGS. 4A-4E depict several illustrations of a crimper die for use in the crimper of FIG. 1, according to an embodiment in accordance herewith.

FIGS. 5A-5E depict several illustrations of another crimper die for use in the crimper of FIG. 1, according to an embodiment in accordance herewith.

DETAILED DESCRIPTION

Specific embodiments of the present disclosure are now described with reference to the figures, wherein like reference numbers indicate identical or functionally similar elements.

The following detailed description describes examples of embodiments and is not intended to limit the present technology or the application and uses of the present technology. Although the description of embodiments hereof is in the context of a crimper, the present technology may also be used in other devices. Furthermore, there is no intention to be bound by any expressed or implied theory presented in the preceding technical field, background, brief summary or the following detailed description.

Embodiments of disclosed herein are directed to a crimper for loading an implantable medical device or appliance onto a delivery device or appliance and converting the implantable medical device from an uncompressed state to a compressed state. In embodiments, the crimper includes two handles or arms that are attached at one end and pivot at the attachment location. The crimper is designed to pivot open to an angle to allow alignment and top loading of the implantable medical device. The crimper includes attachment areas that are positioned at opposing locations on the two handles or arms. The attachment areas allow crimper dies to be attached, whether removably or permanently. The crimper dies operate, in coordination, to create a crimping chamber that increases or decreases in volume as the two handles or arms pivot. The two handles or arms operate as a lever and apply a force, via leverage, to close the crimper and load, via the crimper dies, the implantable medical device onto the delivery device, while converting the implantable medical device from an uncompressed state to a compressed state.

Figure 1:
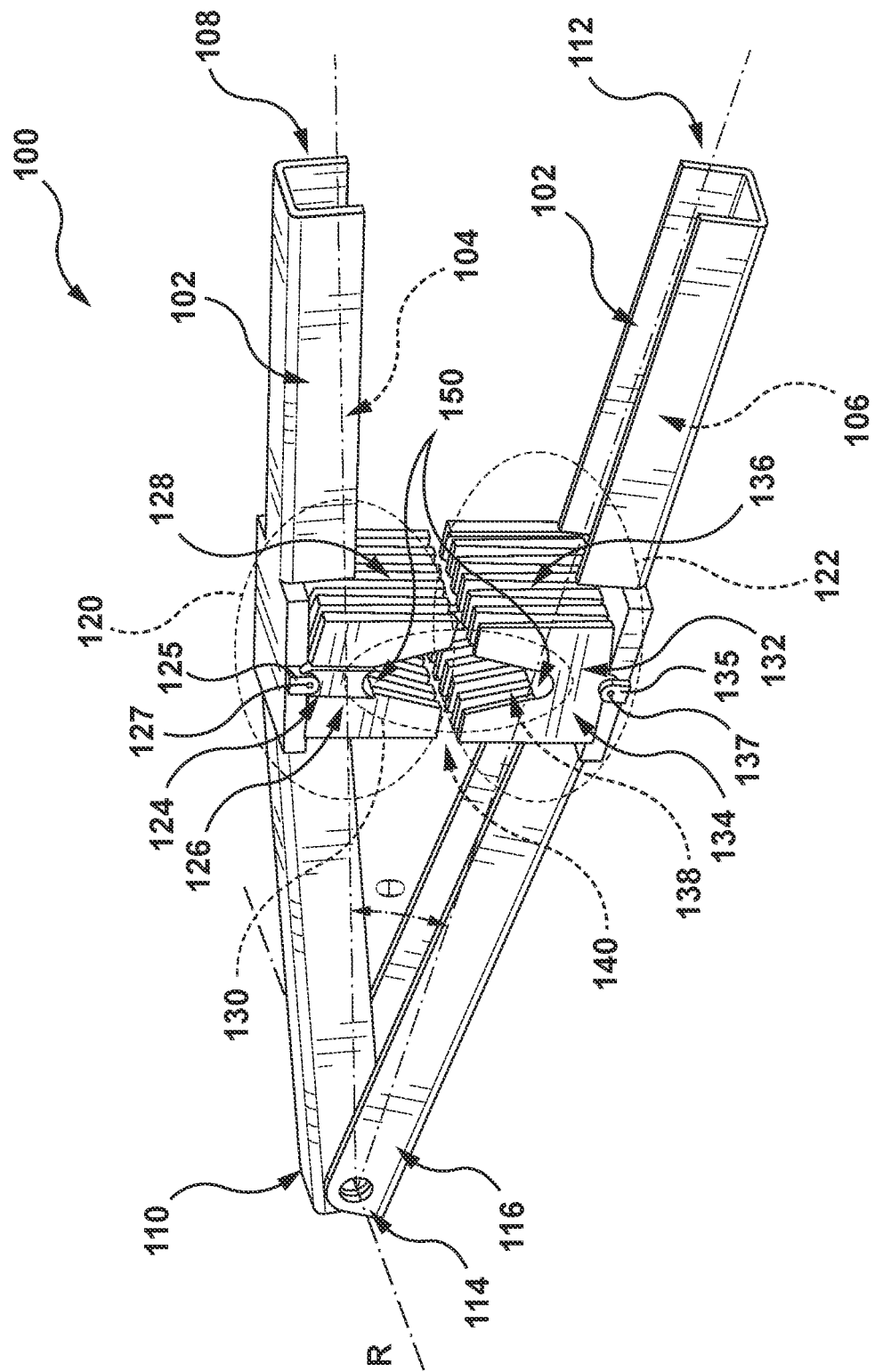
FIG. 1 depicts a perspective illustration of a crimper for use with a medical device, according to an embodiment in accordance herewith.

FIG. 1 illustrates an example of a crimper 100 in accordance with an embodiment hereof. One skilled in the art will realize that FIG. 1 illustrates one example of a crimper and that existing components illustrated in FIG. 1 may be removed and/or additional components may be added to the crimper 100.

As illustrated in FIG. 1, the crimper 100 includes an arm unit 102. The arm unit 102 includes a first arm 104 and a second arm 106. The first arm 104 includes a proximal end 108 and a distal end 110. The second arm 106 includes a proximal end 112 and a distal end 114. The first arm 104 and the second arm 106 are coupled by a pivot connection 116 located at the distal end 110 of the first arm 104 and the distal end 114 of the second arm 106. In embodiments, the pivot connection 116 can include a clevis pin, a bot, a pin, and the like.

In an embodiment, the first arm 104 and the second arm 106 can be separate components that can be removably attached at the pivot connection 116 to form the arm unit 102. In another embodiment, the first arm 104 and the second arm 106 can be a single component that fold toward each other, for instance, via a living hinge therebetween, to form an integrated arm unit 102. The first arm 104 and the second arm 106 can be formed of any suitable material such as, but not limited to aluminum, stainless steel, or a polymeric material.

The first arm 104 and the second arm 106, when coupled, form an approximate V-shape, in which the pivot connection 116 allows an angle, $\theta$, between the first arm 104 and the second arm 106 to be increased or decreased by rotating about an axis of rotation, R. The pivot connection 116 is configured to allow the first arm 104 and the second arm 106 to move relative to each other from an open state to a closed state, as illustrated in FIGS. 2A-2E discussed in detail below. As described herein, an open state for the crimper 100 defines any angle, $\theta$, between the first arm 104 and the second arm 106 that allows a user to insert an implantable medical device and/or delivery device in the crimper 100 and that allows a user to view the insertion to properly align the implantable medical device and the delivery device. As described herein, the closed state defines any angle, $\theta$, between the first arm 104 and the second arm 106 in which the crimper 100 is operating to compress the implantable medical device and to crimp or load the implantable medical device onto a delivery device. For example, in an embodiment, the angle, $\theta$, between the first arm 104 and the second arm 106, when in the open state, can range from approximately 45 degrees to approximately 180 degrees. Likewise, for example, in an embodiment, the angle, $\theta$, between the first arm 104 and the second arm 106, when in closed state, can range between approximately 45 degrees to approximately 0 degrees.

The pivot connection 116 can be any type of mechanical joint or electro-mechanical joint that allows the first arm 104 and the second arm 106 to move relative to each other. For example, the pivot connection 116 can include one or more of a hinge, a rivet, a pivot pin, a pivot joint, an axel, a living hinge, etc. In an embodiment, the pivot connection 116 can include a movement assistance device to provide a force that assists in the movement of the first arm 104 and the second arm 106 relative to each other. For example, the pivot connection 116 can include a spring, strut, a motor, gears, ratchets, etc.

The arm unit 102 includes a first crimper die 120 and a second crimper die 122. The first crimper die 120 and the second crimper die 122 are configured to receive an implantable medical device and alter the implantable medical device from an uncompressed state to a compressed state by the movement of the arm unit 102. Additionally, the first crimper die 120 and the second crimper die 122 are configured to crimp or load the implantable medical device onto a delivery device. In an embodiment, the first crimper die 120 and the second crimper die 122 can be removable from the arm unit 102. As such, the first crimper die 120 and the second crimper die 122 may be interchangeable with other types of crimper dies configured to accommodate different dimensions and/or configurations of implantable medical devices and/or delivery devices. The first crimper die 120 and the second crimper die 122 may be formed of any suitable material such as, but not limited to aluminum, stainless steel, or a polymeric material.

The first crimper die 120 includes a base portion 124, a first row 126 of crimper elements 127, and a second row 128 of crimper elements 127. The crimper elements 127 of the first row 126 are arranged, in a first direction, along a first side of the first crimper die 120. The crimper elements 127 of the second row 128 are arranged, in the first direction, along a second side of the first crimper die 120, wherein the first and second sides are opposing, parallel sides of the first crimper die 120. Each of the crimper elements 127 in the first row 126 are spaced apart a distance in the first direction to create a volumetric space between each of the crimper elements 127 in the first row 126. Likewise, each of the crimper elements 127 in the second row 128 are spaced apart a distance in the first direction to create a volumetric space between each of the crimper element 127 in the second row 128. The volumetric space between the crimper elements 127 of the first crimper die 120 is configured to allow crimper elements from another crimper die, e.g., the second crimper die 122, to intermesh with the crimper elements 127 of the first row 126 and the second row 128 of the first crimper die 120.

Each of the crimper elements 127 in the first row 126 and the second row 128 extends outward from the base portion 124. Each of the crimper elements 127 can be configured with a linear taper that tapers from a larger cross-sectional dimension, in a direction perpendicular the first direction, at the connection to the base portion 124 to a smaller cross-sectional dimension, in a direction perpendicular the first direction, at an outer or free end of each of the crimper elements 127. Due to the tapering, the base portion 124, the first row 126 of the crimper elements 127, and the second row 128 of the crimper elements 127 form a first tapered channel 130 that extends in the first direction. While the components of the first crimper die 120 are described as distinct components, one skilled in the art will realize that one or more of the components of the first crimper die 120 can be formed, manufactured, or constructed as a single piece or unit having the various described features.

The second crimper die 122 includes a base portion 132, a first row 134 of crimper elements 127, and a second row 136 of the crimper elements 127. The crimper elements 127, in the first row 134, are arranged, in a first direction, along a first side of the second crimper die 122. The crimper elements 127 of the second row 136 are arranged, in the first direction, along a second side of the second crimper die 122, wherein the first and second sides are opposing, parallel sides of the second crimper die 122. Each of the crimper elements 127 in the first row 134 are spaced apart a distance in the first direction to create a volumetric space between each of the crimper elements 127 in the first row 134. Likewise, each of the crimper elements 127 in the second row 136 are spaced apart a distance in the first direction to create a volumetric space between each of the crimper element 127 in the second row 136. The volumetric space between the crimper elements 127 of the second crimper die 122 is configured to allow crimper elements from another crimper die, e.g., the first crimper die 120, to intermesh with the crimper elements 127 of the first row 134 and the second row 136 of the second crimper die 122.

Each of the crimper elements 127 in the first row 134 and the second row 136 extends outward from the base portion 132. Each of the crimper elements 127 can be configured with a linear taper that tapers from a larger cross-sectional dimension, in a direction perpendicular the first direction, at the connection to the base portion 132 to a smaller cross-sectional dimension, in a direction perpendicular the first direction, at an outer or free end of each of the crimper elements 127. Due to the tapering, the base portion 132, the first row 134 of the crimper elements 127, and the second row 136 of the crimper elements 127 form a second tapered channel 138 that extends in the first direction. While the components of the second crimper die 122 are describe as distinct components, one skilled in the art will realize that one or more of the components of the second crimper die 122 can be formed, manufactured, or constructed as a single piece or unit having the various described features.

The first crimper die 120 and the second crimper die 122 are coupled to the first arm 104 and the second arm 106, respectively. When coupled, the first crimper die 120 and the second crimper die 122 are positioned opposing each other. The first crimper die 120 and the second crimper die 122 can be attached to the first arm 104 and the second arm 106, respectively, by any method such as, but are not limited to, adhesives, fusing, welding, mechanical connections, and a friction-fit coupling.

In an embodiment, the first crimper die 120 and the second crimper die 122 can be coupled to the first arm 104 and the second arm 106, respectively, by mechanical connections that allow the first crimper die 120 and the second crimper die 122 to move in a direction that is substantially perpendicular to the first direction of the first crimper die 120 and the second crimper die 122. The first arm 104 includes tabs 125 formed on opposing sides the first arm 104. The tabs 125 include a pivot connection 127 that allows the first crimper die 120 to pivot relative to the first arm 104. The pivot connection 127 can be any type of mechanical joint or electro-mechanical joint that allows the first crimper die 120 to move relative to the first arm 104. For example, the pivot connection 127 can include one or more of a hinge, a rivet, a pivot pin, a pivot joint, an axel, a living hinge, etc. Likewise, the pivot connection 127 can be removable to allow the first crimper die 120 to be removed and replaced with other crimper dies (e.g., different configurations of the crimper dies).

The second arm 106 includes tabs 135 formed on opposing sides the second arm 106. The tabs 135 include a pivot connection 137 that allows the second crimper die 122 to pivot relative to the second arm 106. The pivot connection 137 can be any type of mechanical joint or electro-mechanical joint that allows the second crimper die 122 to move relative to the second arm 106. For example, the pivot connection 137 can include one or more of a hinge, a rivet, a pivot pin, a pivot joint, an axel, a living hinge, etc. Likewise, the pivot connection 137 can be removable to allow the second crimper die 122 to be removed and replaced with other crimper dies (e.g., different configurations of the crimper dies).

The first crimper die 120 and the second crimper die 122 are positioned on the first arm 104 and the second are 106, respectively, so that, as the arm unit 102 moves towards the closed position, the crimper elements 127 of the first row 126 of the first crimper die 120 intermesh with the crimper elements 127 of the first row 134 of the second crimper die 122. Likewise, as the arm unit 102 moves towards the closed position, the crimper elements 127 of the second row 128 of the first crimper die 120 intermesh with the crimper elements 127 of the second row 136 of the second crimper die 122. Once the crimper elements 127 intermesh, the first tapered channel 130 of the first crimper die 120 and the second tapered channel 138 of the second crimper die 122 form a crimping chamber 140. As illustrated in FIG. 1, the crimping chamber 140 can define a volume that approximates a rhombohedron. In an embodiment, the base portion 124 of the first crimper die 120 and the base portion 132 of the second crimper die 122 can each include a semi-circular channel or groove 150 formed therein with each being located along an opposing long side of the rhombohedron of the crimping chamber 140.

The first tapered channel 130 of the first crimper die 120 and the second tapered channel 138 of the second crimper die 122 are configured such that a volume of the crimping chamber 140 decreases as the crimper 100 moves through the closed state. In an embodiment that includes the semi-circular channels in the base portion 124 of the first crimper die 120 and the base portion 132 of the second crimper die 122, the crimping chamber 140 transforms into a cylindrical volume when the crimper 100 is in a completely closed state.

While the crimping chamber 140 is described above as defining a rhombohedron shaped volume, one skilled in the art will realize that the shape and dimension of the crimping elements 127 can be changed to create a differently shaped volume as required by the implantable medical device being compressed and positioned. For example, the crimping elements 127 may be configured with a curvilinear taper that forms a cylindrical volume for the crimping chamber 140, when intermeshed.

In embodiments, the crimper 100 operates to convert an implantable medical device from its uncompressed state to its compressed state. Likewise, the crimper 100 operates to crimp or load the implantable medical device onto a delivery device. In operation, the implantable medical device is loaded into one of the first tapered channel 130 of the first crimper die 120 or the second tapered channel 138 of the second crimper die 122 and positioned in a direction that is parallel to the axis of rotation, R, of the arm unit 102. The delivery device can also be positioned and aligned relative to the implantable medical device. The crimper 100 is then moved from the open state to the closed state to convert the implantable medical device from its uncompressed state to its compressed state and load the implantable medical device onto the delivery device.

To operate the crimper 100, a force can be applied to the first arm 104 and the second arm 106. When the force is applied, the first arm 104 and the second arm 106 rotate about the pivot connection 116 towards one another to transition from the open state to the closed state. As the crimper 100 transitions from the open state to the closed state, the first row 126 and the second row 128 of the crimper elements 127 of the first crimper die 120 begin to intermesh with the first row 134 and the second row 136 of the crimper elements 127 of the second crimper die 122 and form the crimping chamber 140. As the crimper 100 continues to transition through the closed state, the volume of the crimping chamber 140 decreases and the intermeshed crimper elements 127 apply a compression force to external surfaces of the implantable medical device. That is, the first row 126 and the second row 128 of the crimper elements 127 of the first crimper die 120 intermesh with the first row 134 and the second row 136 of the crimper elements 127 of the second crimper die 122 such that the first tapered channel 130 and the second tapered channel 138 define the crimping chamber 140 that is configured to crimp the expandable medical device from its uncompressed state to its compressed state. For example, if the implantable medical device is round or cylindrical in shape, the crimper elements 127 the first crimper die 120 and the second crimper die 122 apply a force on the surface of the implantable medical device from various directions as the arm unit 102 transitions through and to the closed state thereby compressing the implantable medical device.

The crimper 100 can be utilized on any type of implantable medical device that requires a conversion from an uncompressed state to a compressed state. In an embodiment, the crimper can be applied to any implantable medical device that requires onsite crimping of the implanted medical device onto a catheter, e.g., organic tissue containing valve repair devices. In an embodiment, the crimper 100 can be used with balloon-expandable stents.

For example, the crimper 100 can be utilized on implantable medical devices that are to be delivered transluminally, e.g., via a catheter, and need to be loaded onto or into a catheter. In this example, the implantable medical device can include a heart valve prosthesis, which includes a stent or frame, and a prosthetic valve attached to the interior of the frame. The stent/frame may be crimped to have a low profile such that the prosthesis can be delivery through the vessels to a target location in a compressed state, and then expanded at the target location, by a balloon of the delivery device, for instance, to replace the native heart valve. By having the crimper 100 open at an angle large enough to view the first crimper die 120 or the second crimper die 122, a user can properly locate and position such a heart valve prosthesis with respect to the catheter. For example, when a balloon catheter with a non-crimped stent/frame of a heart valve prosthesis is placed within the crimper 100, a user can visually ensure that the prosthesis is properly located over the balloon of the catheter before proceeding with the crimping operation.

As described above, the crimper 100 provides a portable solution for compressing and loading implantable medical devices at a location where the medical devices will be implanted. Further, the open, top loading design of the crimper 100 provides increased visibility in loading and aligning the implantable medical devices and the delivery device as well as rapid fine adjustments. Moreover, the V-shaped arm unit being usable with interchangeable sets of crimper dies, i.e., ones tailored to various implantable medical devices, provides a portable, versatile crimping device, which may reduce expected costs of manufacturing the crimper 100. As such, the crimper 100 can provide crimping procedures at a reduced cost and in a portable fashion. Further, the use of removable crimper dies facilitates the ease of assembly. Moreover, the design of the crimper 100 and use of removable crimper dies reduces the work to clean and sterilize the crimper 100.

For example, a heart valve prosthesis is typically loaded onto a delivery device or catheter at the time of the implantation procedure, e.g., at the hospital by hospital staff. The prosthesis needs to be properly aligned and loaded onto the delivery catheter because, if there is an error, the improperly aligned prosthesis may need to be discarded, which is wasteful and costly. The crimper 100 provides a straight-forward and accurate procedure to crimp such a heart valve prosthesis onto a balloon catheter at the hospital.

While the components of the crimper 100 are described above with relative terms "first," "second," "proximal," and "distal," one skilled in the art will realize that the use of these terms is intended only to identify components of the crimper 100 and do not define any preferred or ordinal arrangement of the components of the crimper 100. For example, while the first crimper die 120 is described as being coupled to the first arm 104 and the second crimper die 122 is described as being coupled to the second arm 106, in an embodiment, the second crimper die 120 can be coupled to the first arm 104 and the first crimper die 120 can be coupled to the second crimper arm 106. Likewise, for example, while the implantable medical device is described as being positioned in the second crimper die 122 during operation, in an embodiment, the implantable medical device can be positioned in the first crimper die 120.

FIGS. 2A-2E illustrate an example of the operation of the crimper 100 in accordance with an embodiment hereof. One skilled in the art will realize that FIGS. 2A-2E illustrate one example of the operation of the crimper 100 and that existing components illustrated in FIGS. 2A-2E may be removed and/or additional components may be added to the crimper 100 without departing from the scope of the present invention. Additionally, one skilled in the art will realize that FIGS. 2A-2E illustrate only a few operating states in order to illustrate the operation of the crimper 100, and will realize that the crimper 100 can assume other operational states without departing from the scope of the present invention.

Figure 2A:
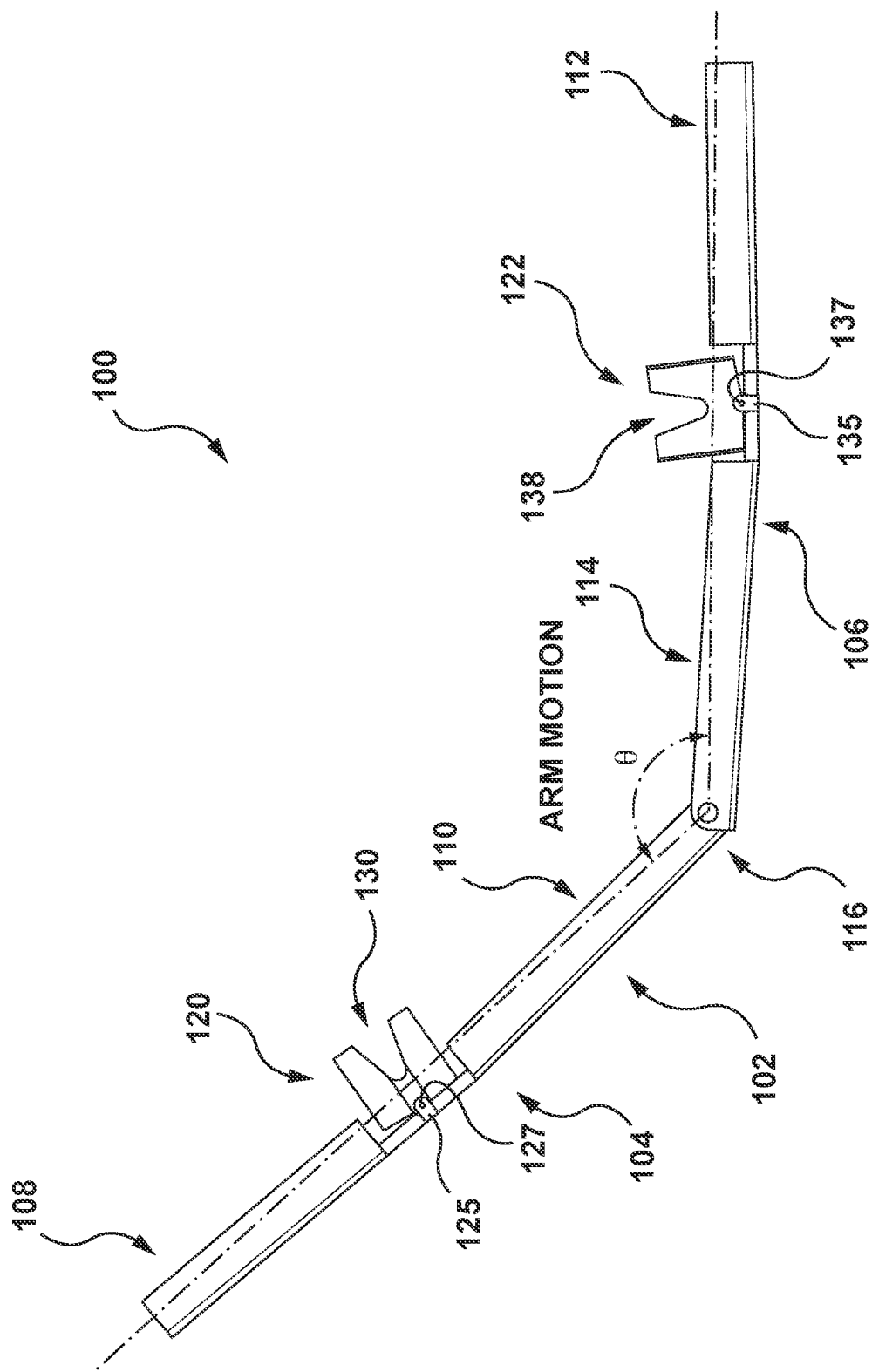
FIGS. 2A-2E depict several illustrations of the operation of the crimper of FIG. 1, according to an embodiment in accordance herewith.

As illustrated in FIG. 2A, to load an implantable medical device, the crimper 100 can be placed to an open state by rotating the first arm 104 and the second are 106 away from each other, in opposite directions, about the pivot connection 116. As noted above, the open state of the crimper 100 may be any position in which the first tapered channel 130 of the first crimper die 120 and/or the second tapered channel 138 of the second crimper die 122 can be viewed and accessed for inserting or placing an implantable medical device and a delivery device.

Figure 2B:
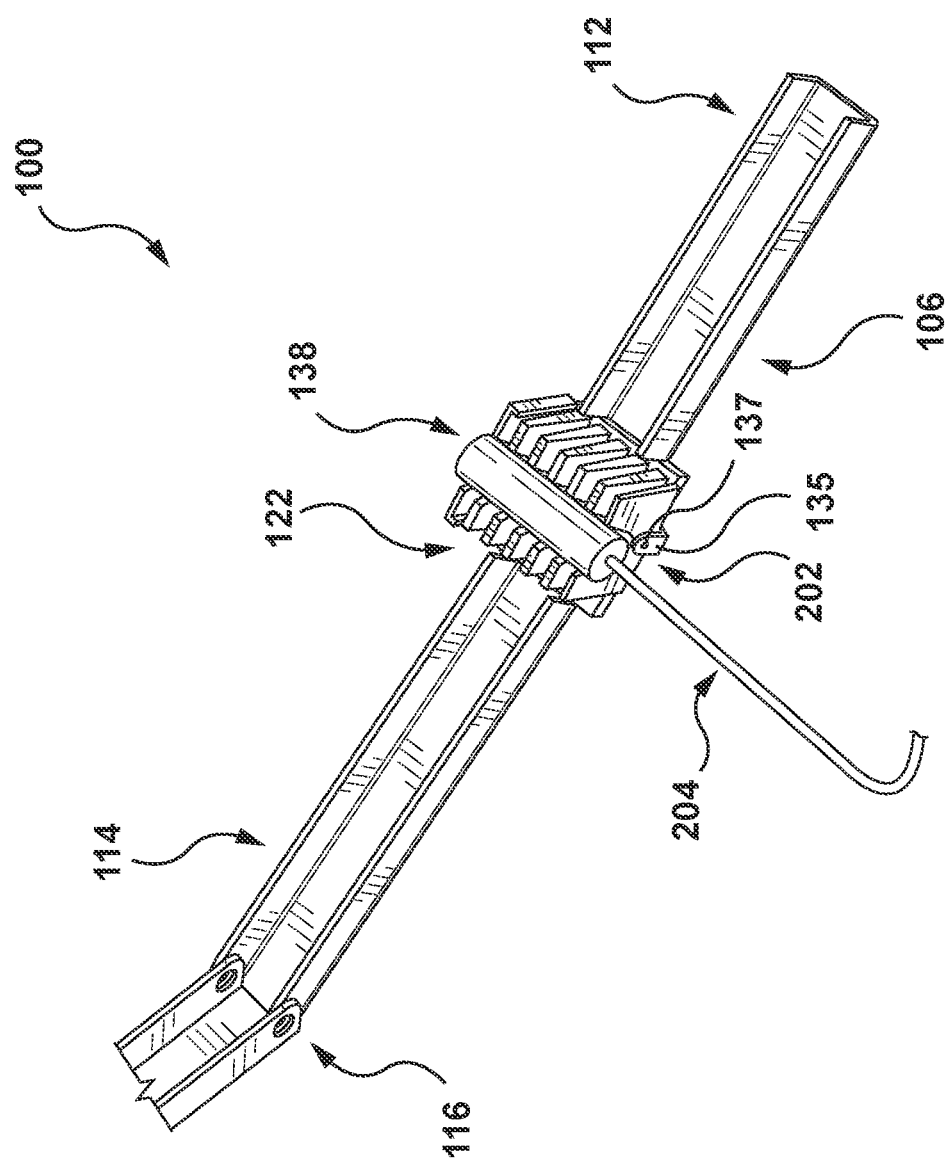

In the open state, the implantable medical device and the delivery device can be loaded into either the first tapered channel 130 of the first crimper die 120 or the second tapered channel 138 of the second crimper die 122. For example, as illustrated in FIG. 2B, an implantable medical device 202 can be placed in the second tapered channel 138 of the second crimper die 122. Likewise, a delivery device 204 can be positioned relative to the implantable medical device 202.

Figure 2C:
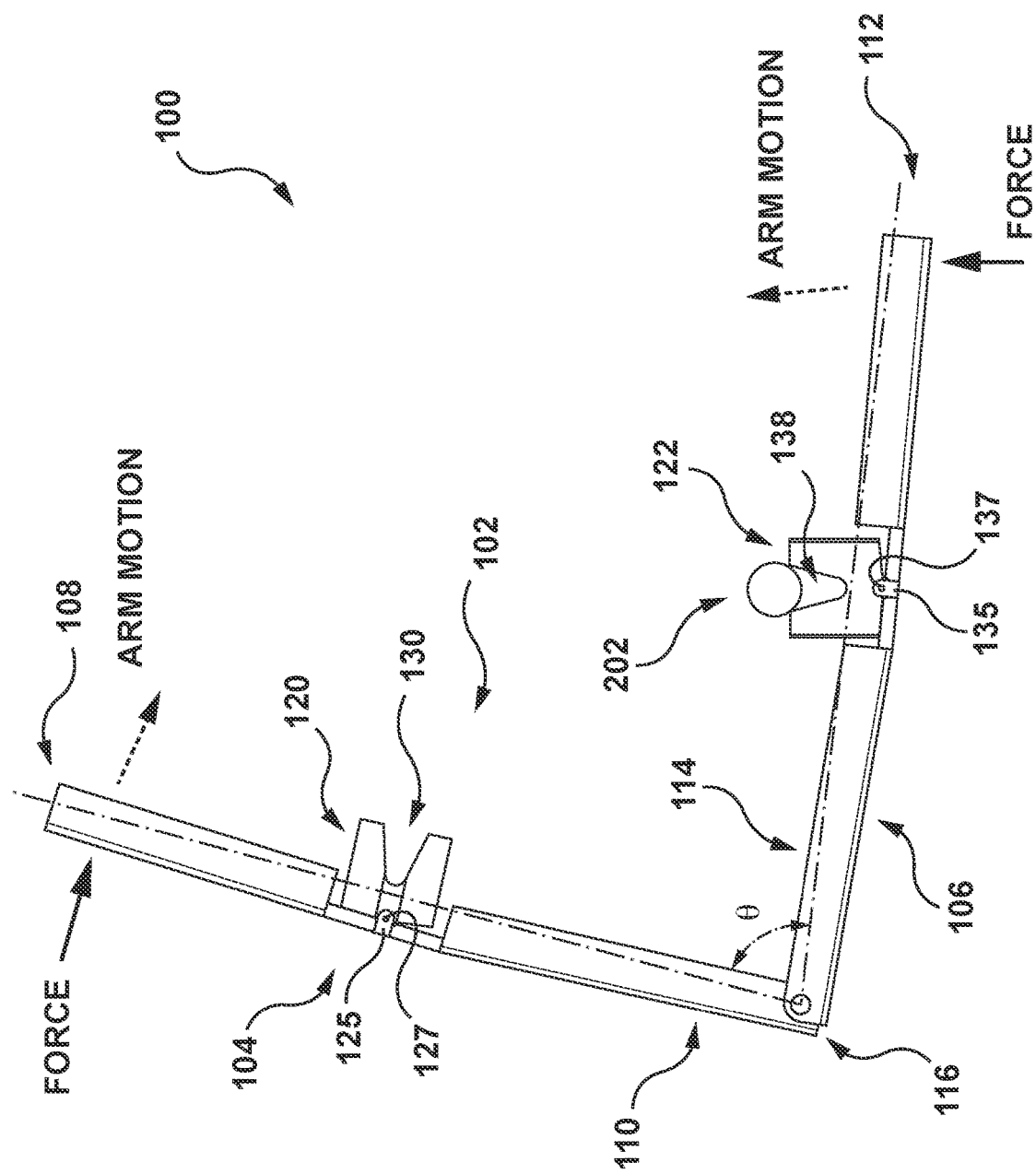
Figure 2D:
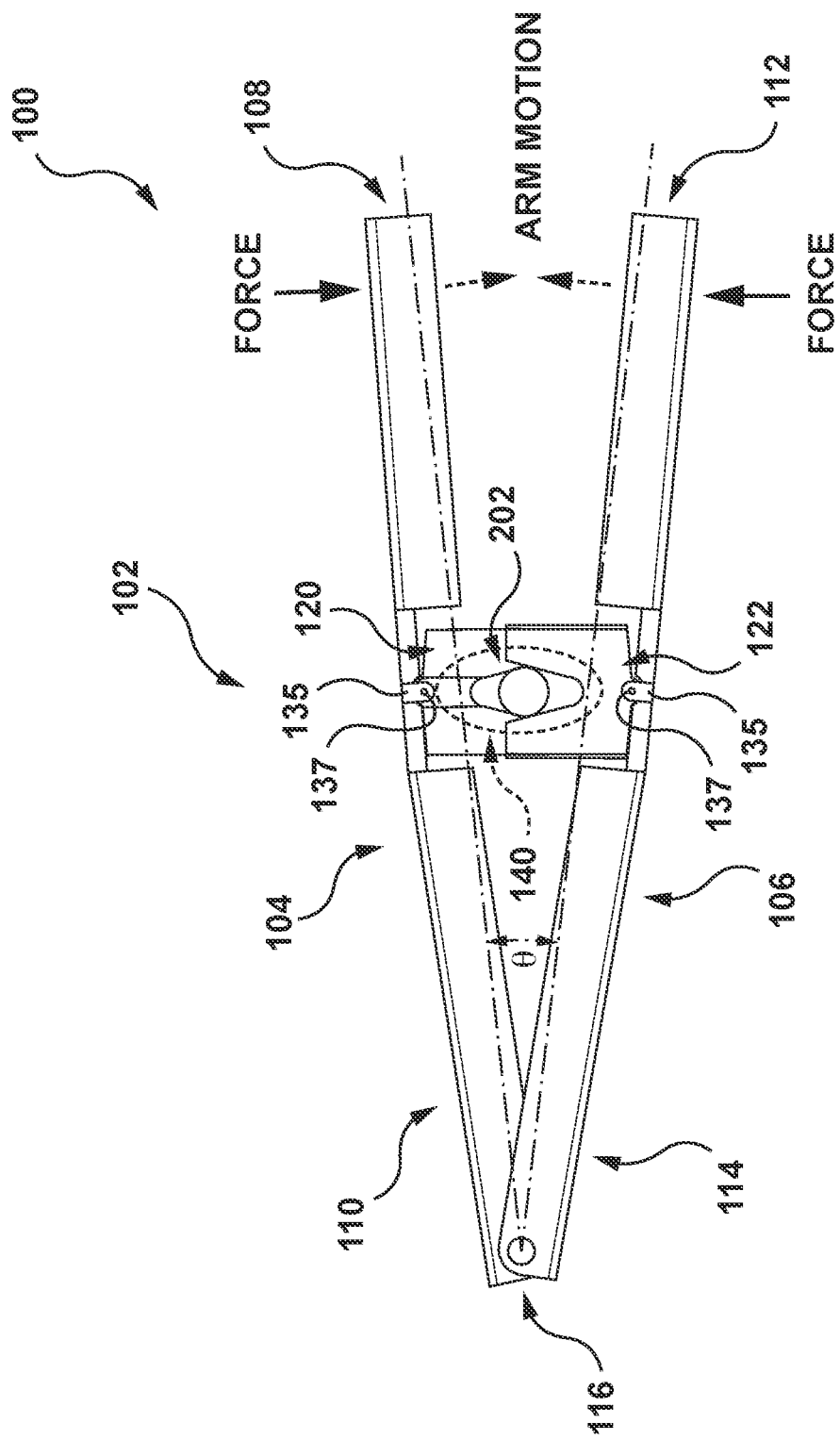

To operate the crimper 100, a force can be applied to one or both of the first arm 104 and the second arm 106. In one example, force can be applied to both arms to move both arms. In another example, the second arm 106 can be held stationery and force can be applied to the first arm 104. In another example, the first arm 104 can be held stationery and force can be applied to the second arm 106. When the force is applied, the first arm 104 and the second arm 106 rotate about the pivot connection 116 towards one another, as illustrated in FIG. 2C. As the first arm 104 and the second arm 106 rotate towards one another, the crimper 100 can enter a partially closed state when the first crimper die 120 and the second crimper die 122 begin to intermesh. As illustrated in FIG. 2D, as the crimper 100 enters the partially closed state, the crimper elements 127 of the first crimper die 120 intermesh with the crimper elements 127 of the second crimper die 122 such that the first tapered channel 130 and the second tapered channel 138 form the crimper chamber 140. As force continues to be applied, the crimper chamber 140 decreases in volume to apply a compression force on the surfaces of the implantable medical device 202.

Figure 2E:
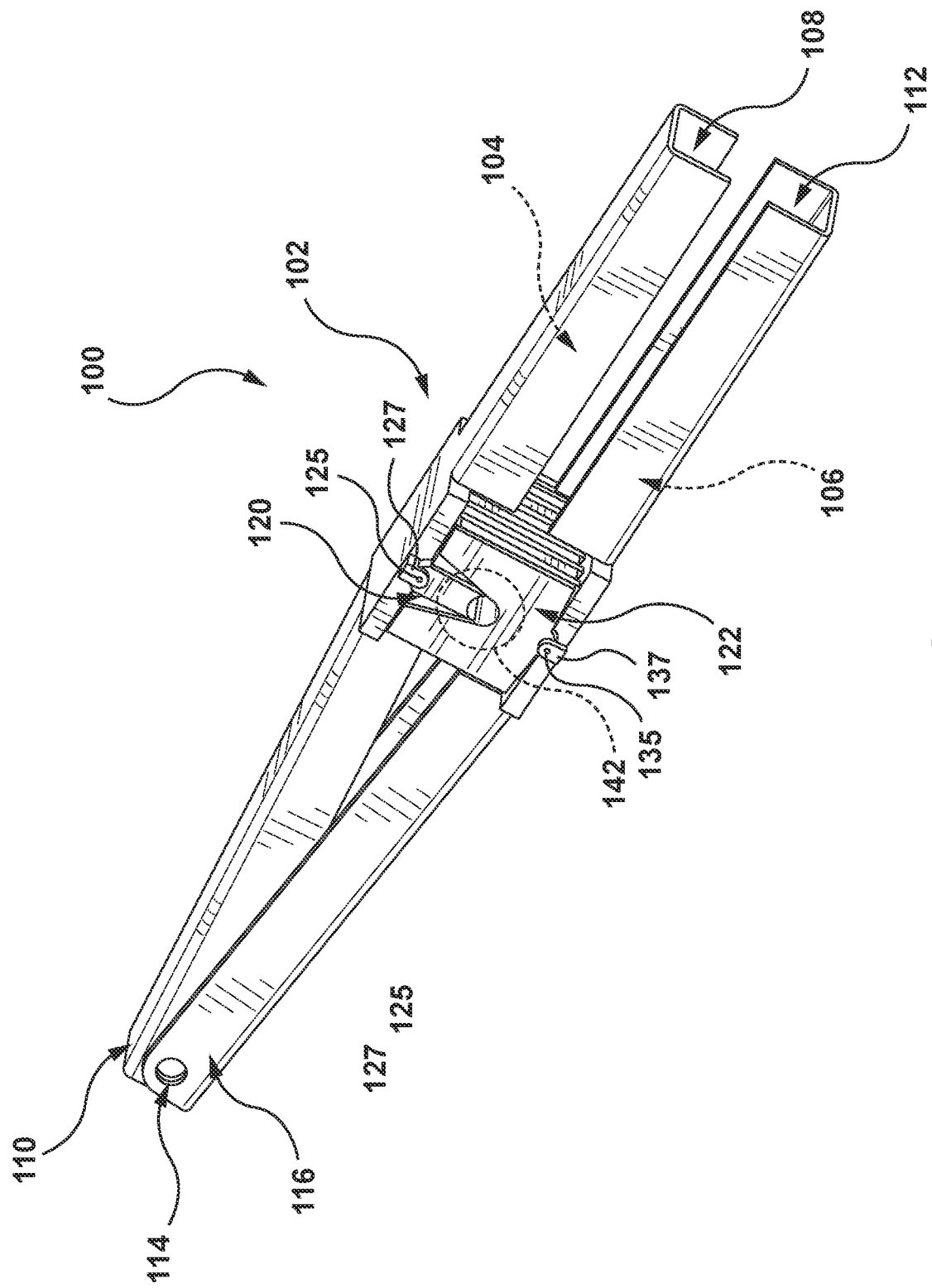

For example, the first crimper die 120 and the second crimper die 122 apply the compression force on the surface of the implantable medical device 202 from various directions as the arm unit 102 transitions from the partially closed state to/through the closed state as illustrated in FIGS. 2D and 2E.

Figure 3A:
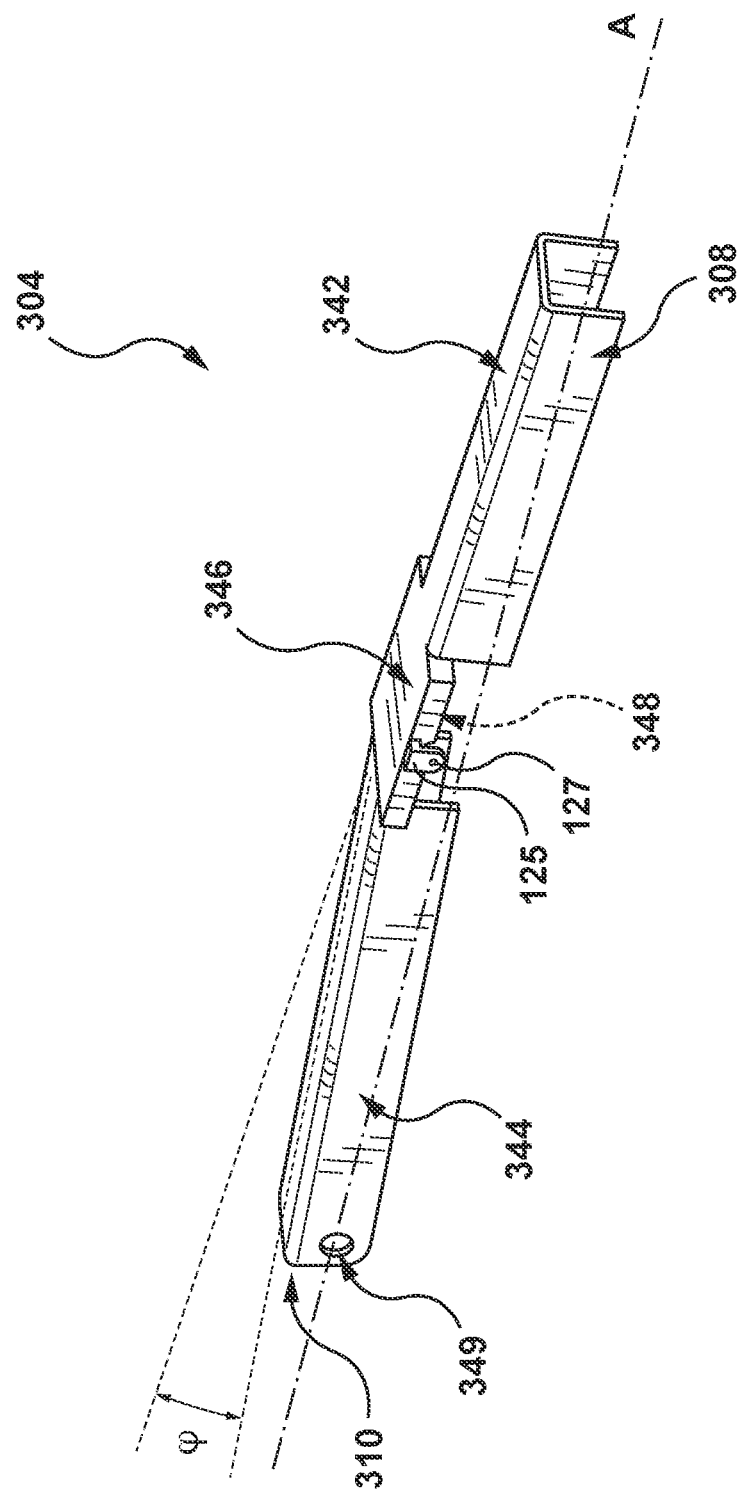
FIG. 3A depicts a perspective illustration of an arm unit for use in the crimper of FIG. 1, according to an embodiment in accordance herewith.
Figure 3B:
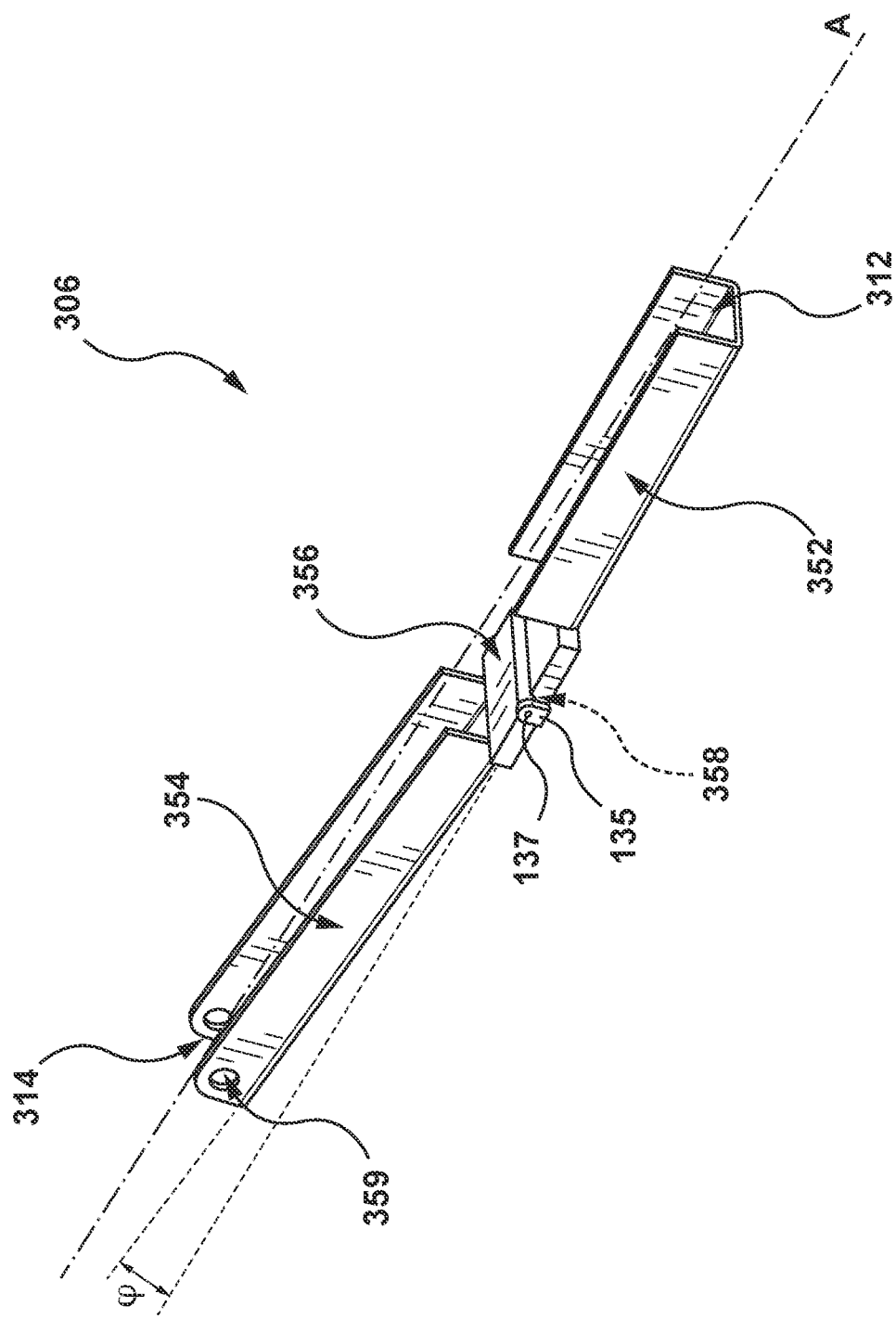
FIG. 3B depicts a perspective illustration of another arm unit for use in the crimper of FIG. 1, according to an embodiment in accordance herewith.

FIGS. 3A and 3B illustrate examples of a first arm 304 and a second arm 306 that can form an arm unit of a crimper device, in accordance with an embodiment hereof. One skilled in the art will realize that FIGS. 3A and 3B illustrate one example of first and second arms and that existing components illustrated in FIGS. 3A and 3B can be removed and additional components can be added to the first arm 304 and the second arm 306.

As illustrated in FIG. 3A, the first arm 304 includes a proximal segment 342, a distal segment 344, and a connecting segment 346. The proximal segment 342 is positioned at a proximal end 308 of the first arm 304. The distal segment 344 is positioned at a distal end 310 of the first arm 304. The connecting segment 346 is positioned between the proximal segment 342 and the distal segment 344.

The connecting segment 346 is configured to receive a crimper die, e.g., the first crimper die 120. In an embodiment, the connecting segment 346 can include a recess channel 348 formed perpendicular to a long axis, A, of the first arm 304. The tabs 125 can be formed at opposing ends of the recess channel 348. The recess channel 348 can be configured to receive a protrusion of the crimper die, e.g., the first crimper die 120. In an embodiment, the recess channel 348, the tabs 125, and the pivot connection 127, and the protrusion of the crimper die can be configured to allow the crimper die to move or tilt during the operation of the crimper 100. For example, the recess channel 348, the tabs 125, and the pivot connection 127, and the protrusion of the crimper die can allow the crimper die to rotate or rock about an axis that extends along the length of the recess channel 348.

The connecting segment 346 can be positioned at an angle, φ, relative to the distal segment 344. The angle, φ, can be configured to create a space for coupling a crimper die such that the crimper dies of the crimper 100 can enter a completely closed state, as illustrated in FIG. 2E. In an embodiment, the angle, φ, can range between approximately 1 degree to approximately 20 degrees.

The distal segment 344 includes one or more pivot slots 349. The pivot slots 349 can be configured to receive a rod, rivet, pin, and or axel to form the pivot connection 116. For example, the pivot slots 349 can be configured as holes to receive a pivot pin to form the pivot connection 116.

In embodiments, the first arm 304 can be formed to any length as required by the particular crimping application. For example, the first arm 304 can be formed to have a length of approximately 12 inches (in). In embodiments, the length of the proximal segment 342 and the distal segment 344 can be selected such that a location of connecting segment 346 is positioned to provide adequate leverage during crimping operations. In any embodiment, the first arm 304 can be formed of any sterilizable, biocompatible material that provides rigidity and strength to the first arm 304, for example, stainless steel, Acrylonitrile Butadiene Styren (ABS), and Delrin.

As illustrated in FIG. 3B, the second arm 306 includes a proximal segment 352, a distal segment 354, and a connecting segment 356. The proximal segment 352 is positioned at a proximal end 312 of the second arm 350. The distal segment 354 is positioned at a distal end 314 of the second arm 350. The connecting segment 356 is positioned between the proximal segment 352 and the distal segment 354.

The connecting segment 356 is configured to receive a crimper die, e.g., the second crimper die 122. In an embodiment, the connecting segment 356 can include a recess channel 358 formed perpendicular to a long axis, A, of the second arm 306. The tabs 135 can be formed at opposing ends of the recess channel 358. The recess channel 358 can be configured to receive a protrusion of the crimper die, e.g., the second crimper die 122. In an embodiment, the recess channel 358, the tabs 135, and the pivot connection 137, and the protrusion of the crimper die can be configured to allow the crimper die to move or tilt during the operation of the crimper 100. For example, the recess channel 358, the tabs 135, and the pivot connection 137, and the protrusion of the crimper die can allow the crimper die to rotate or rock about an axis that extends along the length of the recess channel 358.

The connecting segment 356 can be positioned at an angle, φ, relative to the distal segment 354. The angle, φ, can be configured to create a space for coupling a crimper die such that the crimper dies of the crimper 100 can enter a completely closed state, as illustrated FIG. 2E. In an embodiment, the angle, φ, can range between approximately 1 degree to approximately 20 degrees.

The distal segment 354 includes one or more pivot slots 359. The pivot slots 359 can be configured to receive a rod, rivet, pin, and or axel to form the pivot connection 116. For example, the pivot slots 359 can be configured as holes to receive a pivot pin to form the pivot connection 116.

In embodiments, the second arm 306 can be formed to any length as required by the particular crimping application. For example, the second arm 306 can be formed to have a length of approximately 12 inches (in). In embodiments, the length of the proximal segment 352 and the distal segment 354 can be selected such that a location of connecting segment 356 is positioned to provide adequate leverage during crimping operations. In any embodiment, the second arm 306 can be formed of any sterilizable, biocompatible material that provides rigidity and strength to the first arm 304, for example, stainless steel, ABS, and Delrin.

FIGS. 4A-4E illustrate several views of one example of a first crimper die 420 that can be used with the crimper 100 in accordance with an embodiment hereof. One skilled in the art will realize that FIGS. 4A-4E illustrate one example of the first crimper die 420 and that existing components illustrated in FIGS. 4A-4E can be removed and additional components can be added to the first crimper die 420.

Figure 4A:
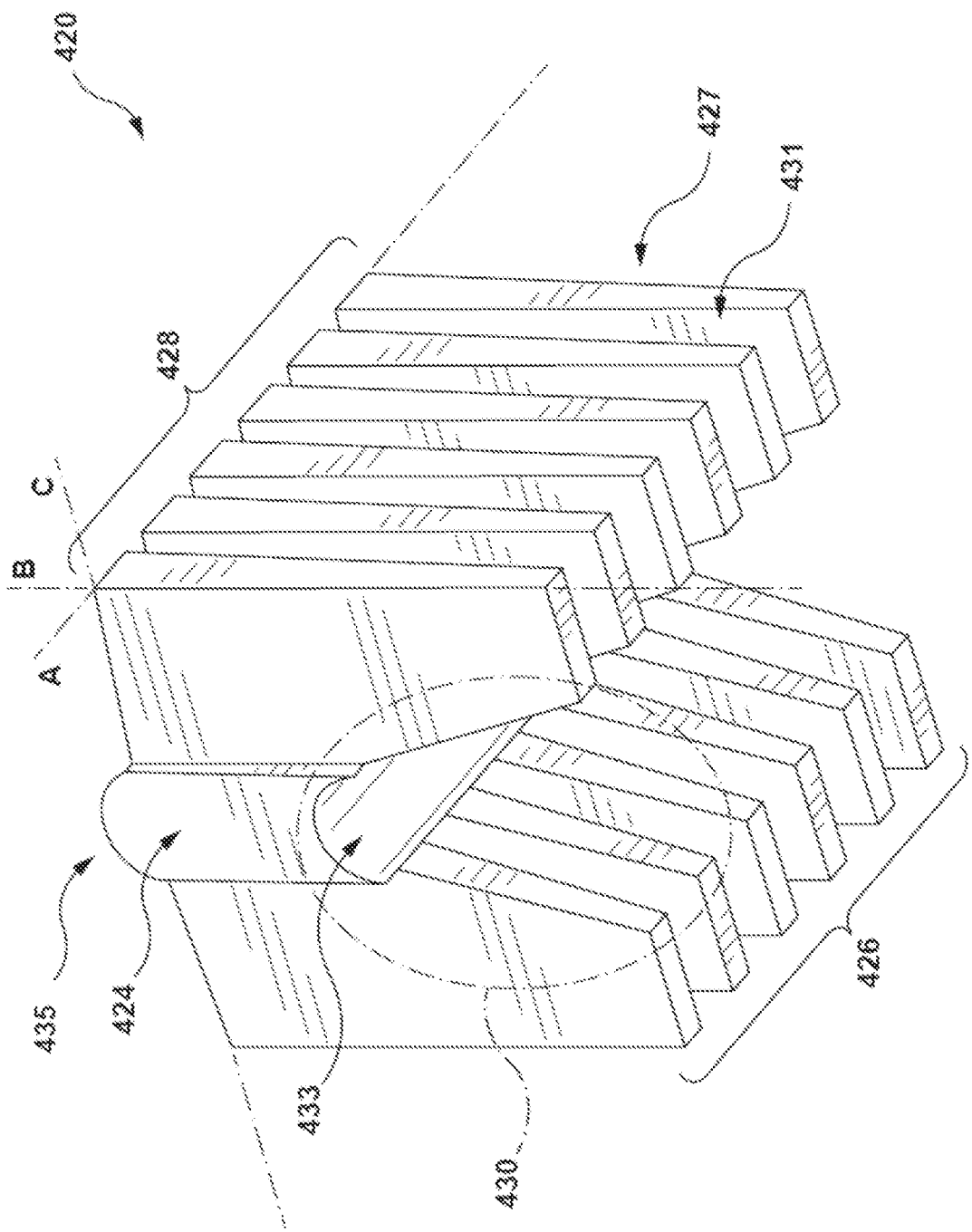

As illustrated in FIG. 4A, the first crimper die 420 includes the base portion 424, the first row 426 of crimper elements 427, and the second row 428 of the crimper elements 427. The base portion 424 can include a semi-circular channel 433 and a protrusion 435. The crimper elements 427 of the first row 426 are arranged in a first direction, A, along a first side the base portion 424. The crimper elements 427 of the second row 428 are arranged in the first direction, A, along a second side of the base portion 424 that opposes or is parallel to the first side. While the components of the first crimper die 420 are describe as distinct components, one skilled in the art will realize that one or more of the components of the first crimper die 427 can be formed, manufactured, or constructed as a single unit.

Each of the crimper elements 427 extends outward from the base portion 424 in second direction, B. Each of the crimper elements 427 in the first row 426 are spaced apart a distance in the first direction, A, to create a volumetric space or recess 431 between each of the crimper elements 427 in the first row 426, as illustrated in FIG. 4B which shows a side view of the first crimper die 420. Likewise, each of the crimper elements 427 in the second row 428 are spaced apart a distance in the first direction, A, to create the volumetric space or recess 431 between each of the crimper element 427 in the second row 428. The volumetric space 431 between the crimper elements 427 is configured to allow crimper elements from another crimper die, e.g., a second crimper die 522 described below, to intermesh with the crimper elements 427 of the first row 426 and the second row 428.

Figure 4C:
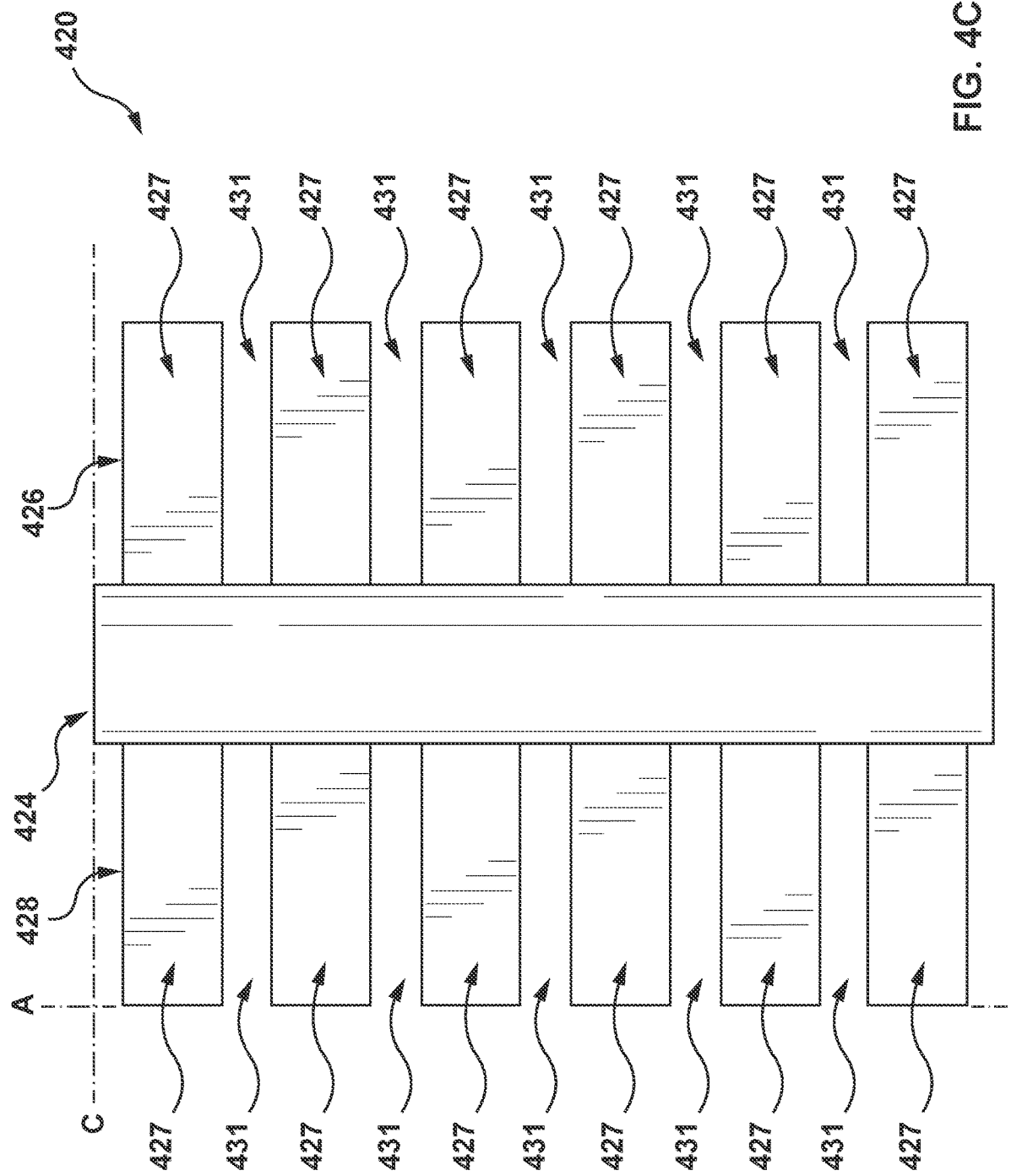

In an embodiment, as illustrated in FIG. 4B, the crimper elements 427 can be configured with a linear taper in the second direction, B, such that the crimper elements 427 taper from a larger cross-sectional dimension, in the first direction, A, at the connection to the base portion 424 to a smaller cross-sectional dimension, in the first direction, A, at an outward or free end of the crimper elements 427, as further illustrated in FIGS. 4C and 4D, which show a top view and a bottom view of the first crimper die 420. That is, as illustrated in FIG. 4B, the crimper element 427 can configured with a trapezoid cross-section in the A-B plane. Likewise, the volumetric spaces 431 can be configured with a corresponding trapezoid cross-section in the A-B plane. While FIGS. 4A-4E illustrate the crimper elements 427 having a linear taper in the second direction B to form a trapezoid shape, one skilled in the art will realize that the crimper elements 427 can have a different taper or no taper. For example, the crimper element 427 can be configured with no taper to define the crimper elements 427 with a square cross-section in the A-B plane and to define the volumetric spaces 431 with a square cross-section in the A-B plane.

Figure 4E:
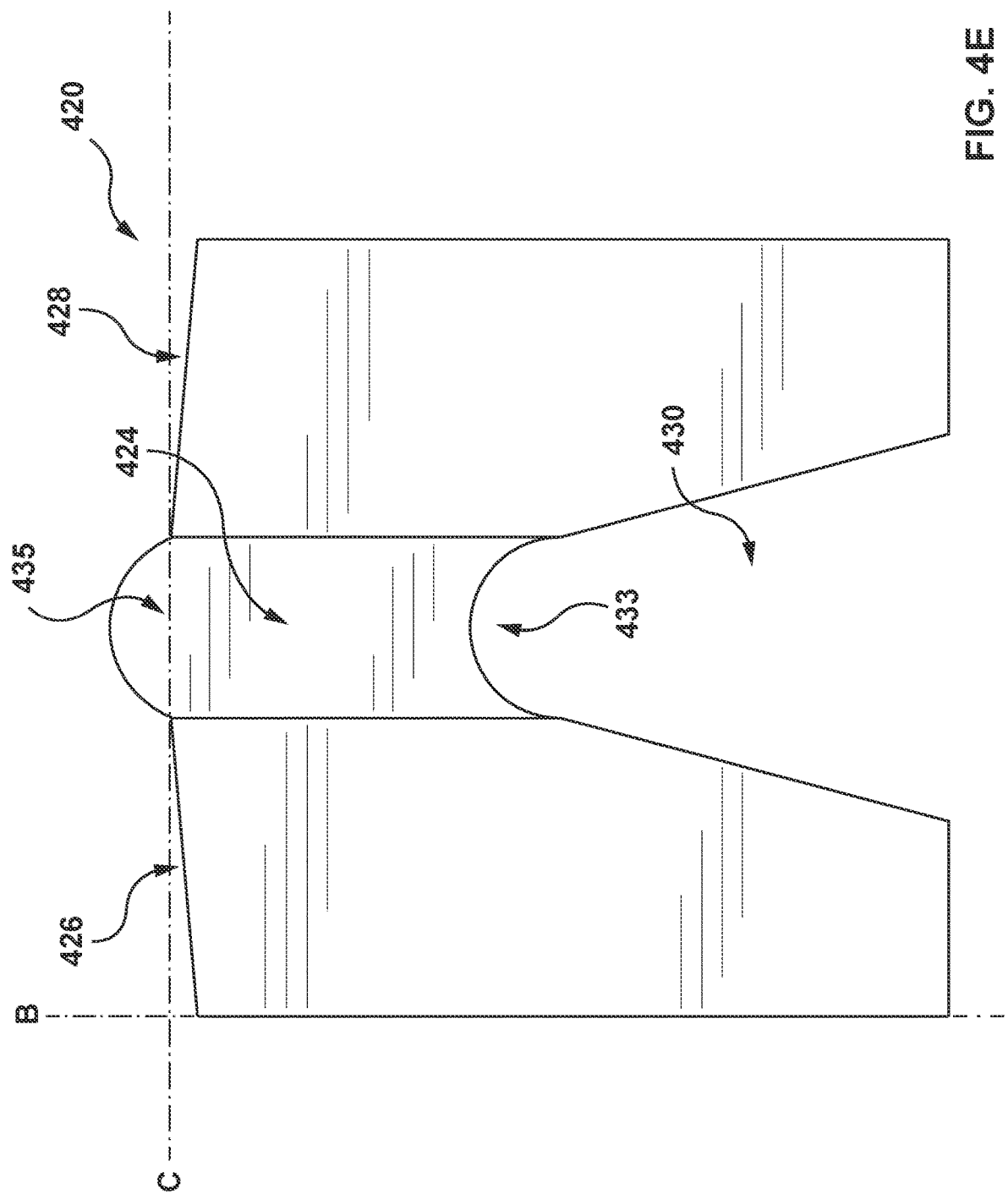

As illustrated in FIGS. 4D and 4E, each of the crimper elements 427 can be configured with a linear taper in the second direction B such that the crimper elements 427 taper from a larger cross-sectional dimension, in a third direction, C, at the connection to the base portion 424 to a smaller cross-sectional dimension, in the third direction, C, at an outward or free end of the crimper elements 427. Due to the tapering, the base portion 424, the first row 426 of the crimper elements 427, and the second row 428 of the crimper elements 427 form a first tapered channel 430 that extends in the first direction, A. As illustrated in FIG. 4E, the first tapered channel 430 can be configured with a V-shape in the B-C plane where the semi-circular channel 433 forms the bottom of the first tapered channel 430.

While the first tapered channel 430 is described above as defining a V-shaped volume, one skilled in the art will realize that the shape and dimension of the crimping elements 427 can be changed to create a differently shaped volume as required by the implantable medical device being compressed and positioned. For example, the crimping element 427 can be configured with a curvilinear taper that forms a cylindrical or semi-circular shaped volume for the first tapered channel 430.

The base portion 424 can include a protrusion 435. The protrusion 435 can operate as the connection point to an arm of the crimper 100. In an embodiment, protrusion 435 can be coupled to an arm of the crimper 100 by mechanical connection that allows the first crimper die 420 to move in a second direction, B. As illustrated in FIG. 4E, the bottom surfaces of the crimper elements 427 (adjacent the protrusion 435) can be tapered or rounded in the second direction, B, to allow the movement of the first crimper die 420.

In embodiments, the first crimper die 420 can be formed to dimensions based on dimensions of the implantable medical device 202 being crimped (e.g., compressed and uncompressed dimensions of the implantable medical device 202). For example, the first crimper die 420 can be formed to dimensions that can receive a 15 millimeter (mm) implantable medical device 202 (e.g., valve/frame) and crimp the implantable medical device to 4 mm. In embodiments, the first crimper die 420 can be formed of any sterilizable, biocompatible material, for example, Delrin, ABS, or nylon.

While the components of the first crimper die 420 are described above with relative terms "first," "second," "proximal," and "distal," one skilled in the art will realize that the use of these terms is intended only to identify components of the first crimper die 420 and do not define any preferred or ordinal arrangement of the components of the first crimper die 420.

FIGS. 5A-5E illustrate several views of one example of a second crimper die 522 that can be used with the crimper 100 in accordance with an embodiment hereof. One skilled in the art will realize that FIGS. 5A-5E illustrate one example of the second crimper die 522 and that existing components illustrated in FIGS. 5A-5E can be removed and additional components can be added to the second crimper die 522.

Figure 5A:
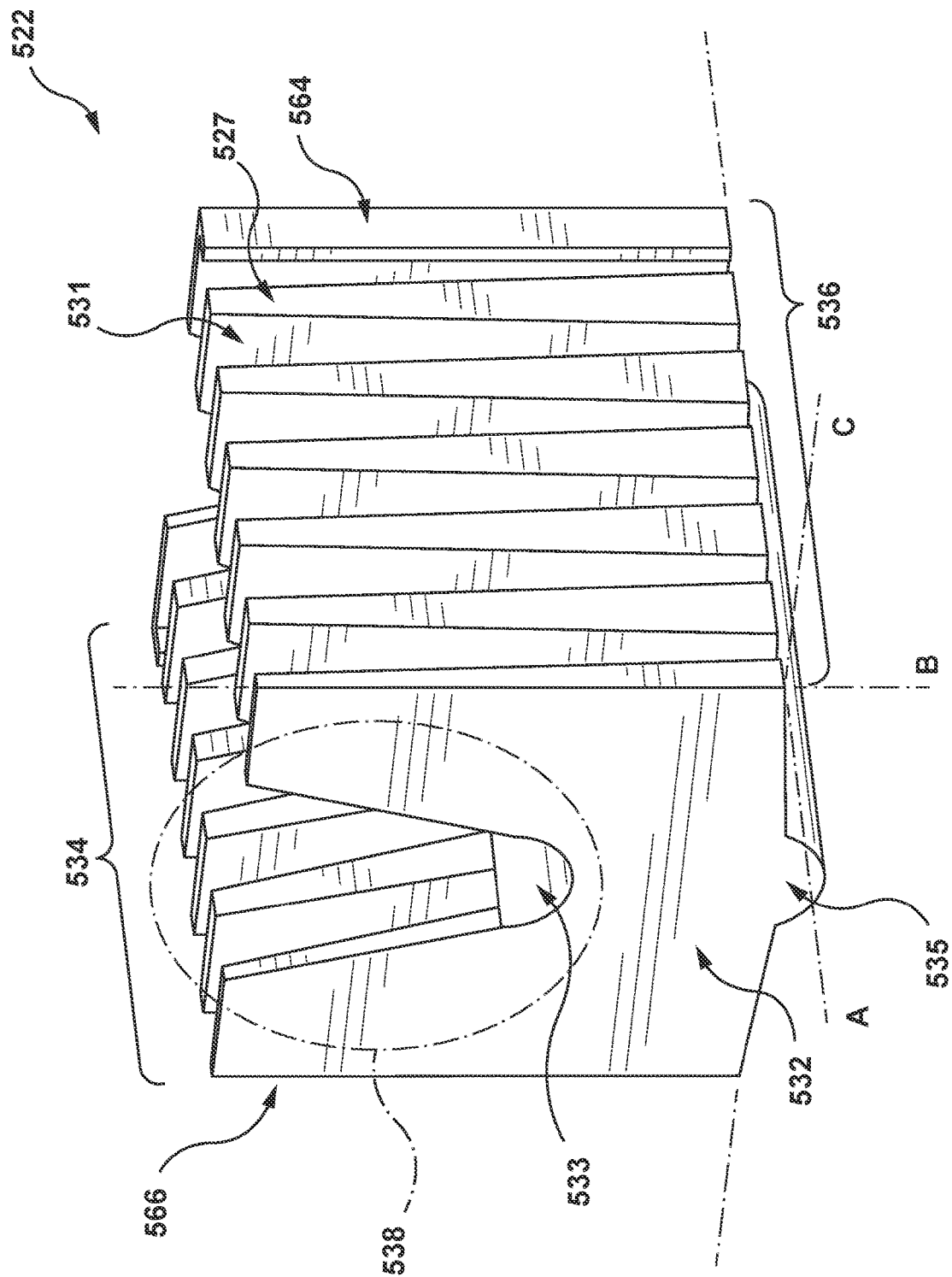

As illustrated in FIG. 5A, the second crimper die 522 includes the base portion 452, the first row 534 of crimper elements 527, and the second row 536 of the crimper elements 527. The base portion 532 can include a semi-circular channel 533 and a protrusion 535. The crimper elements 527 of the first row 534 are arranged in a first direction, A, along a first side of the base portion 532. The crimper elements 527 of the second row 536 are arranged in the first direction, A, along a second side of the base portion 532, with the first and second sides being opposed to each other. The first row 534 and the second row 536 can include first end crimper elements 564 and second end crimper elements 566. The first end crimper elements 564 and the second end crimper elements 566 can operate to interreact with the first crimper die 420 to ensure outer surfaces of the first crimper die 420 and second crimper die 522 remain coplanar and uniform compression is applied to the implantable medical device 202. While the components of the second crimper die 522 are describe as distinct components, one skilled in the art will realize that one or more of the components of the second crimper die 522 can be formed, manufactured, or constructed as a single unit.

Each of the crimper elements 527 extends outward from the base portion 532 in second direction, B. Each of the crimper elements 527 in the first row 534 are spaced apart a distance in the first direction, A, to create a volumetric space or recess 531 between each of the crimper elements 527 in the first row 534, as illustrated in FIG. 5B which shows a side view of the second crimper die 522. Likewise, each of the crimper elements 527 in the second row 536 are spaced apart a distance in the first direction, A, to create the volumetric space or recess 531 between each of the crimper element 527 in the second row 536. The volumetric space or recess 531 between the crimper elements 527 is configured to allow crimper elements from another crimper die, e.g., a first crimper die 420 described above, to intermesh with the crimper elements 527 of the first row 534 and the second row 536.

Figure 5D:
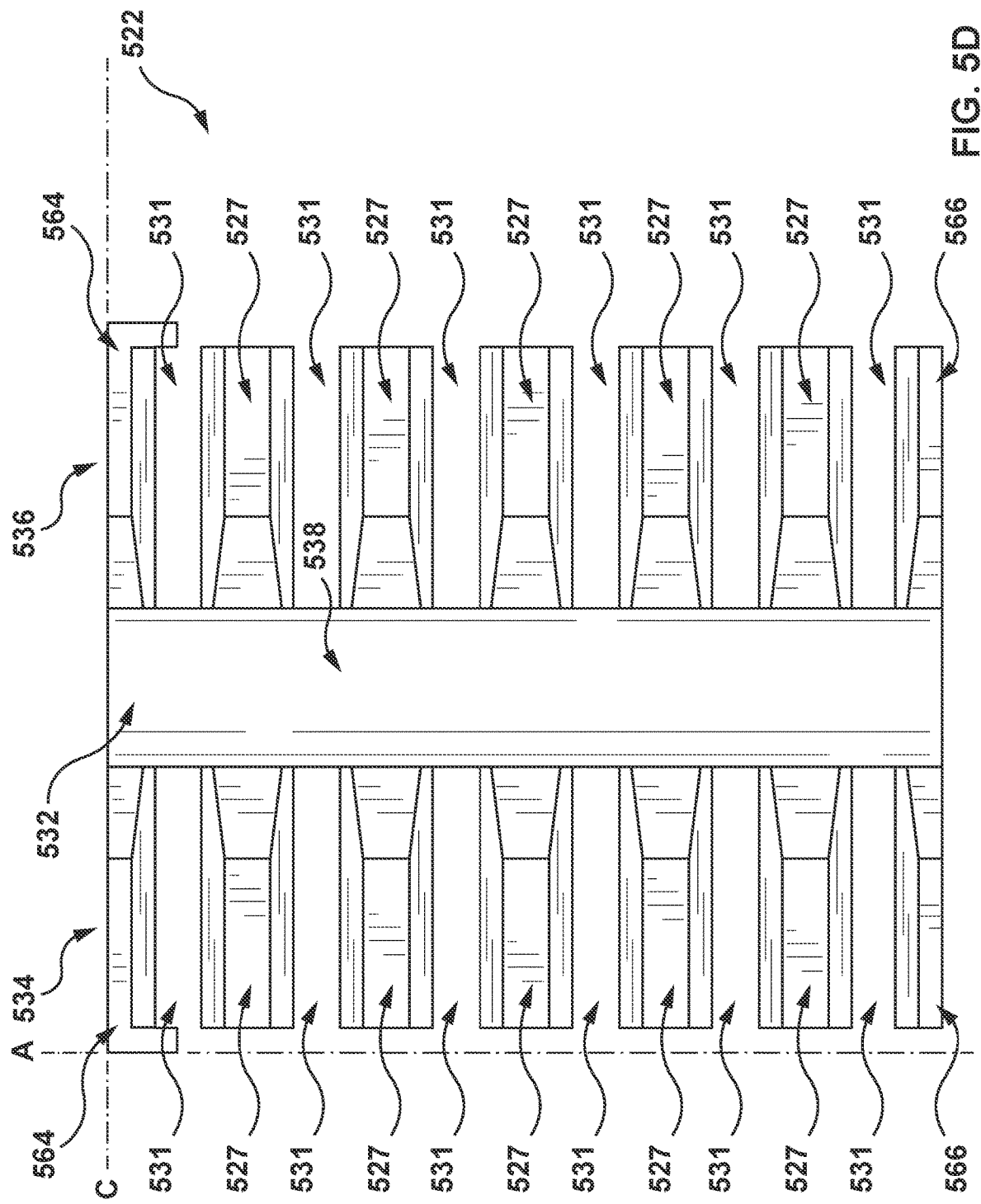

In an embodiment, as illustrated in FIG. 5B, the crimper elements 527 can be configured with a linear taper in the second direction, B, such that the crimper elements 527 taper from a larger cross-sectional dimension, in the first direction, A, at the connection to the base portion 532 to a smaller cross-sectional dimension, in the first direction, A, at an end of the crimper elements 527, as further illustrated in FIGS. 5C and 5D, which show a top view and a bottom view of the second crimper die 522. That is, as illustrated in FIG. 5B, the crimper element 527 can configured with a trapezoid cross-section in the A-B plane. Likewise, the volumetric spaces or recesses 531 can be configured with a corresponding trapezoid cross-section in the A-B plane. While FIGS. 5A-5E illustrate the crimper elements 527 having a linear taper in the second direction B to form a trapezoid shape, one skilled in the art will realize that the crimper elements 527 can have a different taper or no taper. For example, the crimper element 527 can be configured with no taper to define the crimper elements 527 with a square cross-section in the A-B plane and to define the volumetric spaces 531 with a square cross-section in the A-B plane.

Figure 5E:
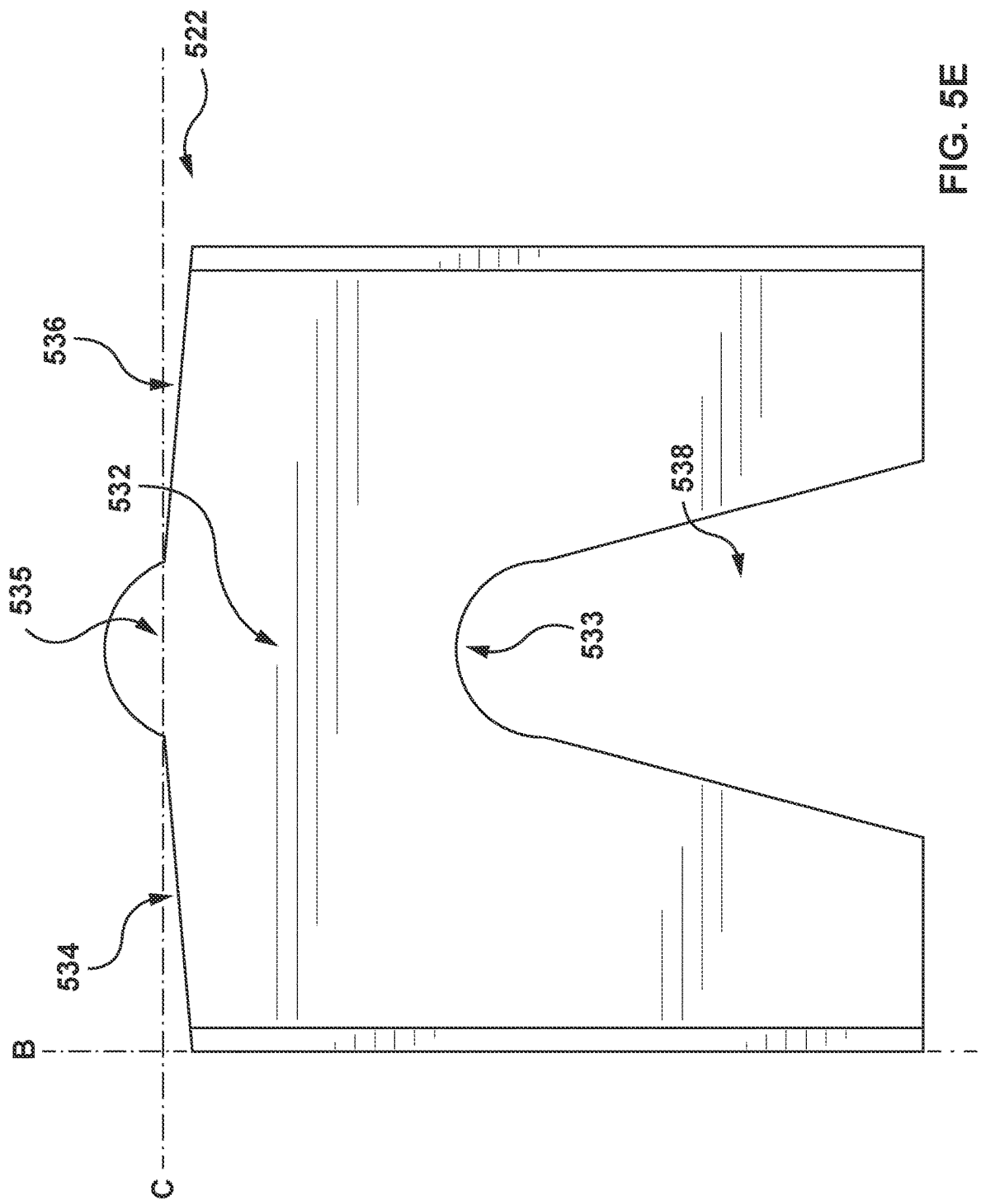

As illustrated in FIGS. 5D and 5E, each of the crimper elements 527 can be configured with a linear taper in the second direction B such that the crimper elements 527 taper from a larger cross-sectional dimension, in a third direction, C, at the connection to the base portion 532 to a smaller cross-sectional dimension, in the third direction, C, at an end of the crimper elements 527. Due to the tapering, the base portion 532, the first row 534 of the crimper elements 527, and the second row 536 of the crimper elements 527 form a second tapered channel 538 that extends in the first direction, A. As illustrated in FIG. 5E, the second tapered channel 538 can be configured with a v-shape in the B-C plane where the semi-circular channel 533 forms the bottom of the first tapered channel 538.

While the second tapered channel 538 is described above as defining a v-shaped volume, one skilled in the art will realize that the shape and dimension of the crimping elements 527 can be changed to create a differently shaped volume as required by the implantable medical device being compressed and positioned. For example, the crimping element 527 can be configured with a curvilinear taper that forms a cylindrical or semi-circular shaped volume for the second tapered channel 538.

The base portion 532 can include the protrusion 535. The protrusion 535 can operate as the connection point to an arm of the crimper 100. In an embodiment, protrusion 535 can be coupled to an arm of the crimper 100 by mechanical connection that allows the second crimper die 522 to move in a second direction, B. As illustrated in FIG. 5E, the bottom surfaces of the crimper elements 427 (adjacent the protrusion 535) can be tapered in the second direction, B, to allow the movement of the second crimper die 522.

In embodiments, the second crimper die 522 can be formed to dimensions based on dimensions of the implantable medical device 202 being crimped (e.g., compressed and uncompressed dimensions of the implantable medical device 202). For example, the second crimper die 522 can be formed to dimensions that can receive a 15 millimeter (mm) implantable medical device 202 (e.g., valve/frame) and crimp the implantable medical device to 4 mm. In embodiments, the second crimper die 522 can be formed of any sterilizable, biocompatible material, for example, Delrin, ABS, or nylon.

While the components of the second crimper die 522 are described above with relative terms "first," "second," "proximal," and "distal," one skilled in the art will realize that the use of these terms is intended only to identify components of the second crimper die 522 and do not define any preferred or ordinal arrangement of the components of the second crimper die 522.

Embodiment 1 is a crimper for altering an expandable medical device from an uncompressed state to a compressed state. The crimper includes a first arm that includes a first crimper die. The first crimper die defines a first tapered channel. The crimper also includes a second arm coupled to the first arm at a pivot connection. The second arm includes a second crimper die that defines a second tapered channel.

The pivot connection enables the first arm and the second arm to rotate about the pivot connection from an open state to a closed state. When the first arm and the second arm are in the open state, the first arm and second arm rotate at an angle relative to one another to allow loading of the expandable medical device into the first tapered channel or the second tapered channel and to allow positioning of the expandable medical device relative to a delivery device. When the first arm and the second arm transition from the open state to the closed state, the first tapered channel and the second tapered channel form a chamber that is configured to crimp the expandable medical device from the uncompressed state to the compressed state.

Embodiment 2 includes the crimper of embodiment 1, wherein the first crimper die includes a base portion, a first row of crimper elements, and a second row of crimper elements, the first row of crimper elements and the second rows of the crimper elements of the first crimper die extending outward from the base portion of the first crimper die to form the first tapered channel, and wherein the second crimper die includes a base portion, a first row of crimper elements, and a second row of crimper elements, the first row of crimper elements and the second rows of the crimper elements of the second crimper die extending outward from the base portion of the second crimper die to form the second tapered channel.

Embodiment 3 includes the crimper of embodiment 2, wherein, for the first crimper die, crimper elements of the first row of crimper elements and crimper elements of the second row of crimper elements are spaced a distance apart in a direction of the first row and second row to form volumetric spaces, the volumetric spaces being configured to receive crimper elements of the second crimper die.

Embodiment 4 includes the crimper of any of embodiments 1-3, wherein, for the second crimper die, crimper elements of the first row of crimper elements and crimper elements of the second row of crimper elements are spaced a distance apart in a direction of the first row and the second row to form volumetric spaces, the volumetric spaces being configured to receive crimper elements of the first crimper die.

Embodiment 5 includes the crimper of any of embodiments 1-4, wherein the chamber formed by the first tapered channel and the second tapered channel includes an approximate rhombohedron shaped cross-section.

Embodiment 6 includes the crimper of embodiment 5, wherein the chamber formed by the first tapered channel and the second tapered channel transitions from the approximate rhombohedron shaped cross-section to an approximate circular cross-section as the first arm and the second arm transition to the closed state.

Embodiment 7 includes the crimper of any of embodiments 1-6, wherein the pivot connection comprises one or more of a pin, a rivet, a screw, an axel, and a bolt.

Embodiment 8 includes the crimper of any of embodiments 1-7, wherein the pivot connection comprises one or more of spring, strut, a motor, gears, or ratchets.

Embodiment 9 includes the crimper of any of embodiments 1-8, wherein the first arm and the second arm are constructed of one or more of stainless steel, Acrylonitrile Butadiene Styren (ABS), or Delrin.

Embodiment 10 includes the crimper of any of embodiments 1-9, wherein the first crimper die and the second crimper die are constructed of one or more of Delrin, Acrylonitrile Butadiene Styren (ABS), or nylon.

Embodiment 11 is a crimper die unit for altering an expandable medical device from an uncompressed state to a compressed state. The crimper die unit includes a first crimper die. The first crimper die includes a base portion, a first row of crimper elements, and a second row of crimper elements. The base portion and the first and second rows of crimper elements of the first crimper die define a first tapered channel, and the first crimper die is configured to be coupled to a movable first arm of an arm unit. The crimper die unit also includes a second crimper die. The second crimper die comprises a base portion, a first row of crimper elements, and a second row of crimper elements. The base portion and the first and second rows of crimper elements of the second crimper die define a second tapered channel. The second crimper die is configured to be coupled to a movable second arm of the arm unit. The first crimper die and the second crimper die are arranged in the arm unit such that, when the arm unit is in an open state, the movable first arm and the movable second arm are positioned at an angle relative to one another to allow loading of the expandable medical device into the first tapered channel or the second tapered channel and to allow positioning of the expandable medical device relative to a delivery device. When the arm unit transitions from the open state to the closed state, the first and second rows of the crimper elements of the first crimper die are arranged to intermesh with the first and second rows of the crimper elements of the second crimper die such that the first tapered channel and the second tapered channel define a chamber that is configured to crimp the expandable medical device from the uncompressed state to the compressed state.

Embodiment 12 includes the crimper die unit of embodiment 11, wherein, for the first crimper die, crimper elements of the first row of crimper elements and crimper elements of the second row of crimper elements are spaced a distance apart in a direction of the first row and second row to form volumetric spaces, the volumetric spaces being configured to receive crimper elements of the second crimper die.

Embodiment 13 includes the crimper of any of embodiments 11 or 12, wherein, for the second crimper die, crimper elements of the first row of crimper elements and crimper elements of the second row of crimper elements are spaced a distance apart in a direction of the first row and the second row to form volumetric spaces, the volumetric spaces being configured to receive crimper elements of the first crimper die.

Embodiment 14 includes the crimper of any of embodiments 11-13, wherein the chamber formed by the first tapered channel and the second tapered channel includes an approximate rhombohedron shaped cross-section.

Embodiment 15 includes the crimper die unit of embodiment 14, wherein the chamber formed by the first tapered channel and the second tapered channel transitions from the approximate rhombohedron shaped cross-section to an approximate circular cross-section as the arm unit transitions to the closed state.

Embodiment 16 includes the crimper of any of embodiments 11-15, wherein, when in the closed state, the chamber defines a volume approximately equal to the compressed state of the implantable medical device.

Embodiment 17 includes the crimper of any of embodiments 11-16, wherein the first crimper die and the second crimper die include protrusions that allow the first crimper die and the second crimper die to move relative to one another.

Embodiment 18 includes the crimper of any of embodiments 11-17, wherein the first crimper die and the second crimper die are constructed of one or more of Delrin, Acrylonitrile Butadiene Styren (ABS), or nylon.

Embodiment 19 is a method for altering an expandable medical device from an uncompressed state to a compressed state. The method includes placing a crimper in an open state where the crimper includes a first crimper die defining a first tapered channel and a second crimper die defining a second tapered channel. In the open state, a top of the first tapered channel or a top of the second tapered channel is exposed for loading the expandable medical device. The method also includes loading the expandable medical device into the first tapered channel or the second tapered channel. Additionally, the method includes transitioning the crimper from the open state to a closed state, where transitioning the crimper from the open state to the closed state, the first tapered channel and the second tapered channel form a chamber that crimps the expandable medical device from the uncompressed state to the compressed state.

Embodiment 20 includes the method of embodiment 19, the method further including positioning the expandable medical device relative to a delivery device in the first tapered channel or the second tapered channel.

It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single device or component for purposes of clarity, it should be understood that the techniques of this disclosure may be performed by a combination of devices or components associated with, for example, a medical device.

What is claimed is:

1. A crimper for altering an expandable medical device from an uncompressed state to a compressed state, the crimper comprising:
    a first arm comprising a first crimper die, the first crimper die defining a first tapered channel having a first arcuate surface; and
    a second arm coupled to the first arm at a pivot connection and comprising a second crimper die defining a second tapered channel having a second arcuate surface, wherein:
        the pivot connection enables the first arm and the second arm to rotate about the pivot connection from an open state to a closed state,
        when the first arm and the second arm are in the open state, the first arm and the second arm are at an angle relative to one another to allow loading of the expandable medical device into the first tapered channel or the second tapered channel and to allow positioning of the expandable medical device relative to a delivery device, and
        when the first arm and the second arm transition from the open state to the closed state, the first tapered channel and the second tapered channel form a chamber defined by the first arcuate surface and the second arcuate surface that is configured to crimp the expandable medical device from the uncompressed state to the compressed state.

2. The crimper of claim 1, wherein the first crimper die comprises a base portion, a first row of crimper elements, and a second row of crimper elements, the first row of crimper elements and the second row of the crimper elements of the first crimper die extending outward from the base portion of the first crimper die to form the first tapered channel, and
    wherein the second crimper die comprises a base portion, a first row of crimper elements, and a second row of crimper elements, the first row of crimper elements and the second row of the crimper elements of the second crimper die extending outward from the base portion of the second crimper die to form the second tapered channel.

3. The crimper of claim 2, wherein, for the first crimper die, crimper elements of the first row of crimper elements and crimper elements of the second row of crimper elements are spaced a distance apart in a direction of the first row and second row to form volumetric spaces, the volumetric spaces being configured to receive crimper elements of the second crimper die.

4. The crimper of claim 3, wherein, for the second crimper die, crimper elements of the first row of crimper elements and crimper elements of the second row of crimper elements are spaced a distance apart in a direction of the first row and the second row to form volumetric spaces, the volumetric spaces being configured to receive the crimper elements of the first crimper die.

5. The crimper of claim 1, wherein the chamber formed by the first tapered channel and the second tapered channel comprises an approximate rhombohedron shaped cross-section.

6. The crimper of claim 5, wherein the first arcuate surface and the second arcuate surface are approximate semi-circles such that the chamber formed by the first tapered channel and the second tapered channel transitions from the approximate rhombohedron shaped cross-section to an approximate circular cross-section as the first arm and the second arm transition to the closed state.

7. The crimper of claim 1, wherein the pivot connection comprises one or more of a pin, a rivet, a screw, an axel, and a bolt.

8. The crimper of claim 1, wherein the pivot connection comprises one or more of a spring, a strut, a motor, gears, or ratchets.

9. The crimper of claim 1, wherein the first arm and the second arm are constructed of one or more of stainless steel, Acrylonitrile Butadiene Styren (ABS), or Delrin.

10. The crimper of claim 1, wherein the first crimper die and the second crimper die are constructed of one or more of Delrin, Acrylonitrile Butadiene Styren (ABS), or nylon.

11. A crimper die unit for altering an expandable medical device from an uncompressed state to a compressed state, the crimper die unit comprising:
    a first crimper die comprising a base portion, a first row of crimper elements, and a second row of crimper elements, wherein:
        the base portion and the first and second rows of crimper elements of the first crimper die define a first tapered channel, and
        the first crimper die is configured to be coupled to a movable first arm of an arm unit; and
    a second crimper die comprising a base portion, a first row of crimper elements, and a second row of crimper elements, wherein:
        the base portion and the first and second rows of crimper elements of the second crimper die define a second tapered channel, and
        the second crimper die is configured to be coupled to a movable second arm of the arm unit, wherein:

the first crimper die and the second crimper die are arranged in the arm unit such that, when the arm unit is in an open state, the movable first arm and the movable second arm are positioned at an angle relative to one another to allow loading of the expandable medical device into the first tapered channel or the second tapered channel and to allow positioning of the expandable medical device relative to a delivery device, and when the arm unit transitions from the open state to a closed state, the first and second rows of the crimper elements of the first crimper die are arranged to intermesh with the first and second rows of the crimper elements of the second crimper die such that the first tapered channel and the second tapered channel define a chamber that is configured to crimp the expandable medical device from the uncompressed state to the compressed state.

12. The crimper die unit of claim 11, wherein, for the first crimper die, crimper elements of the first row of crimper elements and crimper elements of the second row of crimper elements are spaced a distance apart in a direction of the first row and second row to form volumetric spaces, the volumetric spaces being configured to receive crimper elements of the second crimper die.

13. The crimper die unit of claim 12, wherein, for the second crimper die, crimper elements of the first row of crimper elements and crimper elements of the second row of crimper elements are spaced a distance apart in a direction of the first row and the second row to form volumetric spaces, the volumetric spaces being configured to receive crimper elements of the first crimper die.

14. The crimper die unit of claim 11, wherein the chamber formed by the first tapered channel and the second tapered channel comprises an approximate rhombohedron shaped cross-section.

15. The crimper die unit of claim 14, wherein the chamber formed by the first tapered channel and the second tapered channel transitions from the approximate rhombohedron shaped cross-section to an approximate circular cross-section as the arm unit transitions to the closed state.

16. The crimper die unit of claim 11, wherein, when in the closed state, the chamber defines a volume approximately equal to the compressed state of the implantable medical device.

17. The crimper die unit of claim 11, wherein the first crimper die and the second crimper die include protrusions that allow the first crimper die and the second crimper die to move relative to one another.

18. The crimper die unit of claim 11, wherein the first crimper die and the second crimper die are constructed of one or more of Delrin, Acrylonitrile Butadiene Styren (ABS), or nylon.

19. A crimper comprising:
a first arm comprising a first crimper die, and a first pivot connection pivotably connecting the first crimper die to the first arm, the first crimper die defining a first tapered channel; and
a second arm coupled to the first arm at an arm pivot connection, the second arm comprising a second crimper die, and the second crimper die defining a second tapered channel,
wherein:
the arm pivot connection enables the first arm and the second arm to rotate about the arm pivot connection from an open state to a closed state,
when the first arm and the second arm are in the open state, the first arm and the second arm are at an angle relative to one another to allow loading of an expandable medical device into the first tapered channel or the second tapered channel and to allow positioning of the expandable medical device relative to a delivery device, and
when the first arm and the second arm transition from the open state to the closed state, the first tapered channel and the second tapered channel form a chamber that is configured to crimp the expandable medical device from the uncompressed state to the compressed state.

20. The crimper of claim 19, wherein the first arm includes a U-shaped channel, and the first arm further includes a proximal segment, a connecting segment, and a distal segment, wherein the connecting segment can be positioned at an angle relative to the distal segment.

21. The crimper of claim 19, wherein the first arm further includes first tabs formed on opposite sides of the first arm, the first tabs including the first pivot connection.

22. The crimper of claim 19, wherein the first crimper die includes a first protrusion comprising a portion of the first pivot connection.

23. The crimper of claim 19, wherein the first pivot connection comprises one or more of a hinge, a rivet, a pivot pin, a pivot joint, an axle, or a living hinge.

24. The crimper of claim 19, wherein a second pivot connection pivotably connects the second crimper die to the second arm.

25. The crimper of claim 24, wherein the first arm further includes first tabs formed on opposite sides of the first arm, the first tabs including the first pivot connection, and the second arm further includes second tabs formed on opposite sides of the second arm, the second tabs including the second pivot connection.

26. The crimper of claim 24, wherein the first crimper die includes a first protrusion comprising a portion of the first pivot connection, and wherein the second first crimper die includes a second protrusion comprising a portion of the second pivot connection.

27. The crimper of claim 24, wherein the first pivot connection and the second pivot connection comprise one or more of a hinge, a rivet, a pivot pin, a pivot joint, an axle, or a living hinge.

* * * * *